US007466415B2

(12) United States Patent
Gibson et al.

(10) Patent No.: US 7,466,415 B2
(45) Date of Patent: Dec. 16, 2008

(54) METHOD OF PRODUCING MATCHED COATING COMPOSITION AND DEVICE USED THEREFOR

(75) Inventors: Mark Alan Gibson, Bloomfield Township, MI (US); David Lee Griffus, Grand Blanc, MI (US); Allan Blase Joseph Rodrigues, Bloomsfield Hills, MI (US); Michelle Grace Ward, Troy, MI (US)

(73) Assignee: E.I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 10/552,200

(22) PCT Filed: May 6, 2004

(86) PCT No.: PCT/US2004/014371

§ 371 (c)(1),
(2), (4) Date: Oct. 6, 2005

(87) PCT Pub. No.: WO2004/101689

PCT Pub. Date: Nov. 25, 2004

(65) Prior Publication Data

US 2006/0181707 A1 Aug. 17, 2006

Related U.S. Application Data

(60) Provisional application No. 60/468,595, filed on May 7, 2003.

(51) Int. Cl.
*G01J 3/46* (2006.01)
(52) U.S. Cl. .................................................. 356/402
(58) Field of Classification Search ................ None
See application file for complete search history.

(56) References Cited

U.S. PATENT DOCUMENTS

| 3,601,589 | A | * | 8/1971 | McCarty ..................... 382/165 |
| 4,403,866 | A | * | 9/1983 | Falcoff et al. ............... 366/132 |
| 4,773,936 | A | * | 9/1988 | Clark et al. ................. 106/402 |
| 4,813,000 | A | * | 3/1989 | Wyman et al. ............... 382/165 |
| 4,843,574 | A | * | 6/1989 | Gerber ....................... 356/406 |
| 4,853,542 | A | * | 8/1989 | Milosevic et al. ........... 250/353 |
| 4,917,495 | A | * | 4/1990 | Steenhoek ................... 356/328 |
| 5,571,871 | A | * | 11/1996 | Ikeda et al. ................. 525/337 |
| 5,668,633 | A | * | 9/1997 | Cheetam et al. ............. 356/402 |
| 5,751,829 | A | * | 5/1998 | Ringland et al. ............ 382/100 |
| 6,052,195 | A | * | 4/2000 | Mestha et al. ............... 356/425 |
| 6,502,049 | B1 | * | 12/2002 | Takada et al. ............... 702/104 |
| 6,519,038 | B1 | * | 2/2003 | Kritchman .................. 356/425 |
| 6,522,977 | B2 | * | 2/2003 | Corrigan et al. ............. 702/32 |

(Continued)

*Primary Examiner*—Gregory J Toatley, Jr.
*Assistant Examiner*—Gordon J Stock
(74) *Attorney, Agent, or Firm*—Sudhir G. Deshmukh

(57) ABSTRACT

The present invention is directed to a method and device that use spectral measurements of the color of a target coating on a substrate, such as auto body being matched. The method utilizes pigment mixture models to produce a matched coating composition that when applied as a coating matches in appearance with that of the target coating, while also providing other desired coating properties, such as durability, gloss and adhesion. The method of the present invention is well suited for producing automotive refinish paints used in automotive refinish applications wherein the undamaged portion of the autobody is color matched to produce a matched refinish paint that can be then applied over a repaired portion of autobody.

27 Claims, 4 Drawing Sheets

U.S. PATENT DOCUMENTS

| | | | |
|---|---|---|---|
| 6,539,325 B1 * | 3/2003 | Numata et al. | 702/127 |
| 6,577,971 B2 * | 6/2003 | Aitken et al. | 702/81 |
| 6,717,673 B1 * | 4/2004 | Janssen et al. | 356/402 |
| 6,914,613 B2 * | 7/2005 | Marchand et al. | 345/593 |
| 6,957,672 B2 * | 10/2005 | Taylor et al. | 141/83 |

* cited by examiner

METHOD OF PRODUCING MATCHED COATING COMPOSITION AND DEVICE USED THEREFOR

CROSS REFERENCE TO RELATED APPLICATION

This application claims priority from U.S. Provisional application Ser. No. 60/468,595 filed on May 7, 2003, which is incorporated herein by reference.

FIELD OF INVENTION

The present invention generally relates to a method of producing coating compositions that are color matched to target coatings and to a device used therein. The method is specially suited for producing color matched coating compositions suitable for use in the automotive refinish applications.

BACKGROUND OF THE INVENTION

In many industries, particularly in the automotive refinish industry, customers demand not only special color effects and good color match, but also exceptionally good appearance and durability. In refinishing cars in the field, portable colorimeters are commonly used to measure the target color readings off the coating on a car body being repaired, followed by searching through stored databases of paint formulas to find an existing formula that is the closest match with the color readings measured off the car body. Such a process allows a body shop to directly find the best paint formula to match the car being repaired. However, these current processes require creation and maintenance of an extensive database containing thousands of refinish car colors from which one can after exhaustive search select a color match that is closest to the target coating. Moreover, the aforedescribed selection process is expensive since the refinisher has to make and test several paint samples before a close match to the target coating can be achieved. The present invention helps in producing the closest color matches in a cost-effective manner without the need for creating and maintaining an extensive color database.

A method of characterizing a color coating on a surface, such as an auto body, has been disclosed in U.S. Pat. No. 5,231,472. The method utilized measures the reflectance of a reflected light attenuated by the presence of metal flakes typically used in metallic paints. Several solutions to radiative transfer equations of S. Chandrasekhar correlate the attenuated measured reflectances from a target metallic coating with those predicted by the solutions to produce a close color match for the target metallic coating.

STATEMENT OF THE INVENTION

The present invention is directed to a method for producing a matched coating composition for a specified end-use, said method comprising:

(i) measuring reflectances of a target portion of a target coating at a set of preset wavelengths with a spectrophotometer of a coating characterizing device to plot a target spectral curve of said target portion;

(ii) calculating target color (L,a,b or L,C,h) values of said target portion from said target spectral curve of said target portion;

(iii) selecting one or more preliminary colorant combinations from a stored list of known colorants in accordance with a combinatorial selection criteria to match with said target color values;

(iv) determining concentration of each said known colorant in each of said preliminary colorant combinations in accordance with color matching criteria wherein said concentration of each said known colorant is optimized for optimal match of color values of each of said preliminary colorant combinations with said target color values;

(v) balancing said preliminary colorant combinations to allow for the presence of non-colorant components in said matched coating composition to generate one or more viable combinations optimized in accordance with mixing and regulatory criteria developed for said specified end-use; and (vi) selecting an optimal viable combination from said viable combinations in accordance with an acceptability equation for said specified end-use, said optimal viable combination having an optimal acceptability value for said specified end-use wherein said known colorants and non-colorant components when mixed in accordance with said optimal viable combination produce said matched coating composition that when applied as a matched coating visually matches with the appearance of said target coating.

The present invention is further directed to a color characterizing device for producing a matched coating composition for a specified end-use, said device comprising:

(i) a spectrophotometer of said device having a base for positioning said spectrophotometer over a target portion of a target coating;

(ii) means for calculating target color (L,a,b or L,C,h) values of said target portion;

(iii) a computer usable storage medium located in a computer of said device having computer readable program code means residing therein, said computer readable program code means comprising:

(a) means for configuring computer readable program code devices to cause said computer to select one or more preliminary colorant combinations from a stored list of known colorants in accordance with a combinatorial selection criteria to match with said target color space values;

(b) means for configuring computer readable program code devices to cause said computer to determine concentration of each said known colorant in each of said preliminary colorant combinations in accordance with color matching criteria wherein said concentration of each said known colorant is optimized for optimal match of color values of each of said preliminary colorant combinations with said target color values;

(d) means for configuring computer readable program code devices to cause said computer to balance said preliminary colorant combinations to allow for the presence of non-colorant components in said matched coating composition to generate one or more viable combinations optimized in accordance with mixing and regulatory criteria developed for said specified end-use; and (e) means for configuring computer readable program code devices to cause said computer to select an optimal viable combination from said viable combinations in accordance with an acceptability equation for said specified end-use, said optimal viable combination having an optimal acceptability value for said specified end-use wherein said known colorants and non-colorant components when mixed in accordance with said optimal viable combination produce said matched coating composition that when applied as a matched coating visually matches with the appearance of said target coating.

The present invention is still further directed to a method for producing a matched resin for a specified end-use, said method comprising:

(i) measuring reflectances of a target portion of a target substrate at a set of preset wavelengths with a spectrophotometer of a coating characterizing device to plot a target spectral curve of said target portion; (step by user)

(ii) calculating target color (L,a,b or L,C,h) values of said target portion from said target spectral curve of said target portion; (part of step to done by user)

(iii) selecting one or more preliminary colorant combinations from a stored list of known colorants in accordance with a combinatorial selection criteria to match with said target color values; (in device/computer)

(iv) determining concentrations of each said known colorant in each of said preliminary colorant combinations in accordance with color matching criteria to generate one or more intermediate colorant. combinations of said known colorants wherein each of said intermediate colorant combinations is optimized for optimal color match with said target color values;

(v) balancing said intermediate colorant combinations to allow for the presence of non-colorant components in said matched coating composition to generate one or more viable combinations of said known colorants, wherein each of said viable combinations is optimized in accordance with mixing and regulatory practices developed for said specified end-use; and (vi) selecting an optimal viable combination from said viable combinations in accordance with an acceptability equation for said specified end-use, said optimal viable combination having an optimal acceptability value for said specified end-use wherein components in said optimal viable combination when mixed produce said matched resin that when formed as a matched substrate visually matches the appearance of said target substrate.

DETAILED DESCRIPTION OF THE PREFERRED EMBODIMENT

Figure 1:
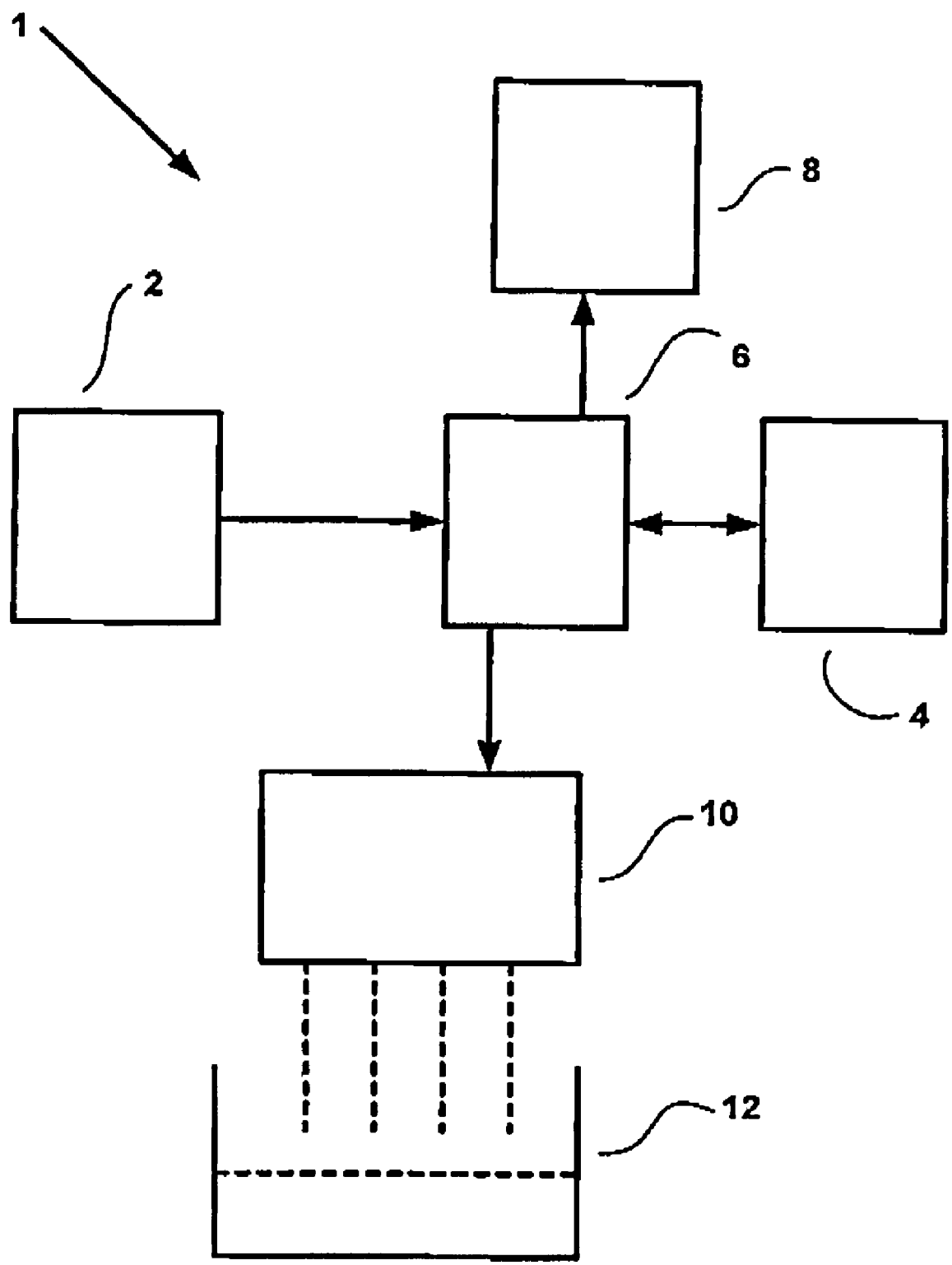
FIG. 1 Is a schematic representation of the various components of a color characterizing device of the present invention.

The terms stated herein are as defined in ASTM Publication designated as E 284-03a, which is published ASTM International, West Conshohocken, Pa.:

Angle of illumination, angle between the specimen normal and the illuminator axis (1991).

Angle of incidence—the angle between a ray impinging on a surface at a point and the perpendicular to the surface at that point. In the description of a beam, the angle of incidence of the ray at the center of the beam.

Absorption coefficient, $\alpha$, —measure of the absorption of radiant energy from an incident beam ($P_0$) as it traverses an absorbing medium according to Bouguer's law, $P = P_0 e^{-\alpha b}$ where b is the sample optical path length (1988).

Angle of reflection, the angle between a ray reflected from a surface at a point and the perpendicular to the surface at that point.

Angle of view, angle between the normal to the surface of the specimen and the axis of the receiver (1988).

Appearance, (1) the aspect of visual experience by which things are recognized. (1990) (2) in psychophysical studies, perception in which the spectral and geometric aspects of a visual stimulus are integrated with its illuminating and viewing environment (1993).

Artificial daylight, an artificial light that has a spectral power distribution approximating that of a phase of natural daylight (1995).

Aspecular, away from the specular direction (1995).

Aspecular angle, viewing angle measured from the specular direction, in the illuminator plane unless otherwise specified (1995). Note-Positive values of the aspecular angle are in the direction toward the illuminator axis.

Attributes of color—(1) for the object mode of appearance, hue, lightness, and saturation. In the Munsell system, Munsell Hue, Munsell Value, and Munsell Chroma. (2) for the illuminant or aperture mode, hue, brightness, and saturation.

Basic color terms, a group of eleven color names found in anthropological surveys to be in wide use in fully developed languages: white, black, red, green, yellow, blue, brown, gray, orange, purple, pink (1990).

Characterize, means to specify the parameters or performance of an instrument or method of measurement. For example, in appearance measurement, the parameters might include the geometric and spectral nature of the illuminator and the receiver, and the performance might be specified by measures of reliability, precision, and bias (1994).

Chroma, (1) attribute of color used to indicate the degree of departure of the color from a gray of the same lightness. See also Munsell chroma (1989). (2) C*, (in the CIE 1976 L*, a*, b* or L*, u* v* system) the quantity $$C^*{}_{ab} = (a^{*2} + b^{*2})^{1/2} \text{ or } C^*{}_{uv} = (u^{*2} + v^{*2})^{1/2} \text{ (1989)}.$$

(3) attribute of a visual perception, produced by an object color that permits a judgment to be made of the amount of pure chromatic color present, irrespective of the amount of achromatic color (1995).

CIE, the abbreviation for the French title of the International Commission on Illumination, Commission Internationale de I"Eclairage.

CIE Spectral tristimulus values, n tristimulus values or color-matching functions of the spectral components of an equal-energy spectrum in the CIE (XYZ) system. The color matching functions are assigned the symbols $\bar{x}(\lambda)$, $\bar{y}(\lambda)$, $\bar{z}(\lambda)$ in the CIE 1931 calorimetric system and $\bar{x}_{10}$, $(\lambda)$, $\bar{y}_{10}(\lambda)$ $\bar{z}_{10}(\lambda)$ in the CIE 1964 supplementary calorimetric system (1990).

CIE 1964 ($x_{10}$, $y_{io}$) chromaticity diagram, n-chromaticity diagram for the CIE 1964 supplementary standard observer, in which the CIE 1964 chromaticity coordinates are plotted, with $x_{10}$ as abscissa and $y_{10}$ as ordinate (1993).

Color, (1) of an object, aspect of object appearance distinct from form, shape, size, position, or gloss that depends upon the spectral composition of the incident light, the spectral reflectance or transmittance of the object, and the spectral, response of the observer, as well as the illuminating and viewing geometry. (1987) (2) perceived, attribute of visual perception that can be described by color names such as white, gray, black, yellow, brown, vivid red, deep reddish purple, or by combinations of such names. Perceived color depends greatly on the spectral power distribution of the color stimulus, but also on the size, shape, structure, and surround of the stimulus area, the state of adaptation of the observer's visual system, and the observers experience with similar observations.

(3) calorimetric, characteristics of a color stimulus denoted by a colorimetric specification with three values, such as tristimulus values. Tristimulus values are sometimes derived on a relative rather than an absolute basis. In this case they may need to be supplemented by the value of a suitable absolute photometric quantity. The appearance of colors depends not only on their absolute tristimulus values, but also on the conditions under which they are viewed, including the nature of the surround; however, colors having the same absolute tristimulus values appear the same in identical viewing conditions. Spectrally different color stimuli can have the same absolute tristimulus values.

Color difference, (1) perceived, the magnitude and character of the difference between two colors described by such terms as redder, bluer, lighter, darker, grayer, or cleaner. (2) computed, the magnitude and direction of the difference between two psychophysical color stimuli and their components computed from tristimulus values, or chromaticity coordinates and luminance factor, by means of a specified set of color-difference equations Color match, (1) condition existing when colors match within a specified or agreed tolerance. Sometimes called commercial color match. Compliance with tolerances can be determined instrumentally or visually. If the test for compliance is visual, physical color tolerance standards may be used for reference. (2) condition existing when colors are indistinguishable; a normal observer is usually implied. Sometimes called an exact color match (1988)

Color matching, procedure for providing, by selection, formulation, adjustment, or other means, a trial color that is indistinguishable from, or within specified tolerances of, a specified standard color under specified conditions (1988).

Complementary colors, color stimuli that produce a specified achromatic stimulus when they are suitably mixed in an additive manner.

Gloss, angular selectivity of reflectance, involving surface-reflected light, responsible for the degree to which reflected highlights or images of objects may be seen as superimposed on a surface. (See also distinctness-of-image gloss, haze (in reflection), luster, sheen, specular gloss.)

Gonioapparent, pertaining to change in appearance with change in illumination angle or viewing angle.

Hiding power, (1) the ability of a coating material to hide the surface coated by producing a specified opacity. (2) the area over which a specified volume of paint can be spread to produce a specified contrast, $C_c$, between areas where the substrate is black and where it is white.

Illuminant, radiant flux that may be specified by its spectral power distribution, and that can, in illuminating objects, affect their perceived colors.

Match, means to provide, by selection, formulation, adjustment, or other means, a trial color that is indistinguishable from, or within specified tolerances of, a specified standard color under specified conditions (1991).

Metallic, pertaining to the appearance of a gonioapparent material containing metal flakes.

Metameric, (1) pertaining to spectrally different objects or color stimuli that have the same tristimulus values (1988). (2) pertaining to objects, having different spectrophotometric curves that match when illuminated by at least one specific spectral composition and observed by a specific observer. (See also parameric) (1988).

Metamerism, property of two specimens that match under a specified illuminator and to a specified observer and whose spectral reflectances or transmittances differ in the visible wavelengths. See also illuminant metamerism, observer metamerism, paramerism. As a consequence of the required difference, the two specimens may not match under a different illuminator or to a different observer. Similar considerations apply to two lights matching to a specified observer but not to other observers, metamerism indices (1991).

Metamers, (1) spectrally different objects or color stimuli $_c$ that have the same—stimulus values (1988).

Reflectance, $\rho$, ratio of the reflected radiant or luminous flux to the incident flux in the given conditions. The term reflectance is often used in a general sense or as an abbreviation for reflectance factor. Such usage may be assumed unless the above definition is specifically required by the context (1989).

Shade, (1) a color produced by a dye or pigment mixture including black dye or pigment. See also shade, v; tint, n; tint, v. (2) an expression of color difference from a reference dyeing such that another dye must be added to produce a match. (3) a color slightly different from a reference color. "Shade" is the most overworked of the terms used to describe colors and color differences in terms of colorant technology, sometimes even being used as a general synonym for "color."

Shade, means to adjust the color of a test specimen to be a closer color match to the standard. Also tint (1990).

Spectral, (1) modifying a quantity, descriptor that the quantity is a function of wavelength; (2) for radiometric quantities, pertaining to monochromatic radiant energy at a specified wavelength or, by extension, to radiant energy within a narrow wavelength band about a specified wave-length.

Spectrophotometry, quantitative measurement of reflection or transmission properties as a function of wavelength.

Specular, pertaining to flux reflected from the surface of an object, without diffusion, at the specular angle (1988).

Specular angle, n-the angle of reflection equal and opposite to the angle of incidence. In gonioapparent phenomena, this definition assumes an illuminator subtending a small angle (1995).

Tint, a color produced by the mixture of white pigment or paint with a chromatic pigment or paint. A tint of a chromatic color is, therefore, lighter and less saturated than the chromatic color. (See shade)

Tristimulus values-amounts of three specified stimuli required to match a color. In the CIE system, they are assigned the symbols X, Y, and Z. (See also CIE spectral tristimulus values.)

Viewing conditions, the conditions under which a visual observation is made, including the angular subtense of the specimen at the eye, the geometric relationship of source, specimen, and eye, the photometric and spectral character of the source, the photometric and spectral character of the field of view surrounding the specimen, and the state of adaptation of the eye.

Wavelength, X of an electromagnetic wave, the distance in the direction of propagation between nearest points at which the electric vector has the same phase (See also complementary wavelength, dominant wavelength) (1990).

The present invention is suited to expeditiously color match the target coating, such as an undamaged portion of an autobody, in a typical automotive collision repair shop environment. The method of the present invention substantially automates the color matching process even under the varying conditions typically experienced in the collision repair shops. In a typical collision repair shop, the d portion of an autobody is repaired, sanded and primed before a coating composition is applied, such as by spraying, dip coating, roller coating or with a brush. By matching the color of a coating composition with the undamaged portion of an autobody, one can use a very small amount of matched coating composition to paint the repaired portion of the autobody. As a result, the cost of auto repair can be minimized while still visually matching the repaired portion of the autobody with the undamaged portion of the autobody.

Broadly stated, in the method of the present invention, the color of the target coating is read by a spectrophotometer (preferably portable), the spectral measurement is transmitted to a computer, an optimum paint formula is determined with the pigment mixture models and printed out or displayed on the computer screen for the shop to weigh and spray. All steps between the measurement and the receipt of the formula are transparent to the user.

While this invention is preferably used in a refinish auto body shop, it can be also used for color matching in other suitable areas, such as matching coatings on plastic substrates or colored plastic substrates; marine substrates, such as ship hulls; aluminum substrates, such as aircraft bodies, matching architectural coatings; textile fibers, fabrics, and non-woven fabrics; and on paper. It could also be used in a laboratory environment with a less skilled work force. The portability of the device of the present invention makes the invention ideal for use in the field.

A method of the present invention is directed to producing a matched coating composition for a specified end-use that visually matches in appearance with a target portion of the target coating. Some of the specified uses can include automotive refinish coatings applied over autobodies, automotive OEM finishes, architectural coatings, industrial coatings, powder coatings, aviation coatings, marine coatings, commercial and residential appliances coatings. The foregoing includes coatings applied over a variety of substrates, such as steel, aluminum, wood, plastic resins, glass, paper, textile fibers, fabrics, non-woven fabrics and cement.

Step (i) of the method of the present invention includes measuring reflectances of a target portion of a target coating applied by means of a spectrophotometer of a coating characterizing device of the present invention. Any suitable spectrophotometer, such as Model MA68II or Model SP64 manufactured by X-Rite, Grandville, Mich. can be used. Portable spectrophotometers are preferred as they can be readily positioned over coated substrate surfaces of various shapes and sizes. If desired one can measure the reflectances over several portions of the target coating to average out the reflectances of the target coating. In a typical spectrophotometer, a light beam of known intensity can be directed towards the target portion and reflectance from the target potion is sequentially measured at at least one, preferably at three, aspecular angles at preset wavelengths. Alternatively, a light beam of known intensity can be sequentially directed at at least one, preferably at three, incident angles towards the target portion and reflectance from the target portion is then measured at preset wavelengths with a single detecting device so as to provide measurements at different aspecular angles, depending on the angle of illumination. Gonioapparent colors should be measured at multiple angles, preferably 3 to 5. For solid colors, a single aspecular angle is sufficient, typically 45 degrees. A common practice for solid colors is to illuminate at a single angle and measure the diffuse reflectance using an integrating sphere, capturing the light reflected at all angles from the target portion. The reverse method of illuminating diffusely and measuring at a single angle yields equivalent results. Diffuse reflectance is preferred when the target portion has a textured surface.

Color has long been measured through the use of spectrophotometers, which measure the percentage of light reflected at each wavelength over the visible region of the electromagnetic spectrum. Typically these readings are taken at 10 nm intervals from 400 nm to 700 nm. A plot of the percent reflectance as a function of wavelength is referred to as a "spectral curve". By way of example, Table 1 shows reflectances of the target portion measured at wavelengths in visible spectrum, ranging from 400 nanometers to 700 nanometers at 10 nanometer intervals with an X-Rite MA68II spectrophotometer wherein the target portion was illuminated at 45° to the normal and the reflectance was measured at the normal angle. For a solid color (non-flake or non-gonioapparent color, such as that lacking metallic flakes), only one spectral curve is typically sufficient to measure solid color properties. Other common geometries of measurement are diffuse illumination with 0° or 8° viewing or the reverse. If a target portion having a metallic color, i.e., gonioapparent color was being matched, reflectance measurements at additional angles would be necessary. ASTM E-2194 recommends three angles, 15°, 45°, and 110° as measured away from the specular reflection. DIN 6175-2 recommends up to five angles, all within this same range of angles. The X-Rite MA68II can provide measurements at 15°, 25°, 45°, 75°, and 110°.

Step (ii) of the method of the present invention comprises calculating target color values of the target portion from the target spectral curve of the target portion. Several alternate equations have been developed to reduce spectral values to numbers indicative of the way a human observer sees the color under a given lighting condition. These are commonly expressed as L,a,b or L,C,h values.

From a spectral curve, one can determine the hue of a color represented by the peak of the curve, e.g., the spectral curve of a blue color would peak in blue wavelengths. A light color would reflect more light across the spectrum and a darker color would reflect less light. A high chroma color would have a reasonably sharper peak and reflect considerably less light at other wavelengths. A low chroma color would have a curve with little difference between peak and trough. Grays would tend to be very flat. Thus a qualitative assessment of the color is possible from a spectral curve. However, color as seen by a human observer is dependent not only on the spectral curve of the color but also the spectral characteristics of the light source under which it is viewed and the spectral sensitivity of the observer. The human eye has three sensors for color vision-a red sensor (X), a green sensor (Y) and a blue sensor (Z). In 1931, the International Committee on Illumination (CIE) standardized the mapping of color in a three-dimensional X, Y, Z space, allowing for the spectral characteristics of the color, the light source and the observer. However it is still difficult to visualize a color from its tristimulus values X, Y, Z. Also, these values do not provide a visually uniform three-dimensional mapping of color. The tristimulus values X, Y, Z can be calculated though the following matrix equation:

$$\bar{t} = \overline{TER} \tag{A}$$

$\bar{t}$=vector of tristimulus values X, Y, Z $\overline{T}$=vector of standard observer weighting functions, which can be obtained from E-308 publication of the American Society of Testing & Materials (ASTM).

$\overline{E}$=vector of relative spectral energy distribution of the light source functions, which can be obtained from ASTM E-308. Illuminant $D_{65}$, representing daylight is commonly used.

R̄=vector of reflectance values

The foregoing X, Y and Z tristimulus values can be more conveniently expressed by using mathematical transformations to "uniform color space" known as L,a,b values, which are described in Theory and Implementation of Modern Techniques of Color Conception, Matching and Control by A. B. J. Rodrigues at Fifth International Conference in Organic Coatings Science and Technology Proceedings, Vol. 3, Advances in Organic Coatings Science and Technology Series, p. 273-275, (1979). The aforementioned reference is hereby incorporated herein by reference. The L,a,b values of the color describes the position of the color. The L,a,b values of each color are a three dimensional rendering of color space in Cartesian coordinates in which a Lightness axis (L*), a red-green axis (a*), and a yellow-blue axis (b*), are described by the following equations:

$$L^* = 116(Y/Y_0)^{1/3} - 16 \quad (1)$$

$$a^* = 500[(X/X_0)^{1/3} - (Y/Y_0)^{1/3}] \quad (2)$$

$$b^* = 200[(Y/Y_0)^{1/3} - (Z/Z_0)^{1/3}] \quad (3)$$

For $X/X_0$, $Y/Y_0$, $Z/Z_0 > 0.008856$ (For $D_{65}$ at 10°, $X_0 = 94.825$, $Y_0 = 100.000$ and $Z_0 = 107.381$).

For $X/X_0$, $Y/Y_0$, $Z/Z_0 < 0.008856$, $L^* = 903.3 (Y/Y_0)$.

The cube root functions in the equations for a*, b* are replaced by the following corresponding functions:

$$f(X/X_0) = 7.787(X/X_0) + 0.1379$$

$$f(Y/Y_0) = 7.787(Y/Y_0) + 0.1379$$

$$f(Z/Z_0) = 7.787(Z/Z_0) + 0.1379$$

In the foregoing equations, $X_0$, $Y_0$ and $Z_0$ are the tristimulus values of a perfect white color for a given illuminant; and X, Y and Z are the tristimulus values for the color to be evaluated. Thus, the L,a,b values are obtained by mathematically integrating the spectral reflectance curve of the color with the spectral distribution of the light source, typically, Illuminant D65, and the spectral sensitivities of the receptors in the human eye, all published in tables listed in ASTM Standard E-308. The foregoing integration process allows characterizing the color through three parameters, generally referred to by X, Y, and Z. The foregoing mathematical transformations readily allow conversion of X, Y, Z to the easier to understand L,a,b values.

Table 1 below shows the spectral reflectance and the L, a, b values of the color of the target portion. L=30.62 indicates that it was a medium to dark color; a=49.87 indicates that it was a fairly saturated red and b=28.57 indicates that it had a yellow shade red.

TABLE 1

| Wavelength in nanometers | Reflectance of Target Portion |
| --- | --- |
| 400 | 0.0320 |
| 410 | 0.0330 |
| 420 | 0.0290 |
| 430 | 0.0250 |
| 440 | 0.0200 |
| 450 | 0.0160 |
| 460 | 0.0140 |
| 470 | 0.0120 |
| 480 | 0.0110 |
| 490 | 0.0100 |
| 500 | 0.0098 |
| 510 | 0.0098 |
| 520 | 0.0098 |

TABLE 1-continued

| Wavelength in nanometers | Reflectance of Target Portion |
| --- | --- |
| 530 | 0.0100 |
| 540 | 0.0100 |
| 550 | 0.0110 |
| 560 | 0.0130 |
| 570 | 0.0180 |
| 580 | 0.0370 |
| 590 | 0.0960 |
| 600 | 0.1880 |
| 610 | 0.2730 |
| 620 | 0.3240 |
| 630 | 0.3500 |
| 640 | 0.3650 |
| 650 | 0.3730 |
| 660 | 0.3790 |
| 670 | 0.3820 |
| 680 | 0.3840 |
| 690 | 0.3860 |
| 700 | 0.3870 |
| L | 30.62 |
| a | 49.87 |
| b | 28.57 |

An acceptable alternative to L,a,b values are the L,C,h values obtained by transforming the color values expressed in Cartesian coordinates into cylindrical coordinates to provide more accurate and uniform representation of the color difference ($\Delta E$) between the target color and the color that matches the target color by using CIE94 or CMC equation. These equations are known and are disclosed in Berns, R. S., "Billmeyer and Saltzman's Principles of Color Technology", $3^{rd}$. Ed., pgs. 120-121, and pages. 117-118, John Wiley & Sons, Inc., which is incorporated herein by reference. The CIE94 equation utilizes the L,a,b values and converts them into the L,C,h values by using the following equations.

L,a,b for target coating and matched compositions can be calculated by using Equations 1, 2 and 3, and color differences $\Delta L$, $\Delta a$, $\Delta b$ are determined by taking into account the differences between the target coating and matched coating. These differences may be determined for different light sources. In L,C,h values, the "C" is determined by the equation below:

$$\text{Chroma} = C^* = \sqrt{a^{*2} + b^{*2}} \quad (4)$$

and the "h" value is determined by the equation below:

$$\text{Hue} = h = \tan^{-1}(b^*/a^*) \quad (5)$$

h is also known as the hue angle

Differences in the color of the target and matched coating are expressed as:

$$\Delta L^* = L^*_b - L^*_s$$

$$\Delta a^* = a^*_b - a^*_s$$

$$\Delta b^* = b^*_b - b^*_s$$

$$\Delta C^* = C^*_b - C^*_s$$

(subscripts s and b in the foregoing equations refer to the target and matched coatings).

Total color difference $\Delta E^*$ between the target and matched coatings is given by:

$$\Delta E^* = \sqrt{\Delta L^{*2} + \Delta a^{*2} + \Delta b^{*2}} \quad (6)$$

$\Delta H^* = k\sqrt{\Delta E^{*2} - \Delta L^{*2} - \Delta C^{*2}}$ (Also referred to as the metric hue difference).

The general equation that expresses the color difference between the target and matched coatings is given by:

$$\Delta E = \left[\left(\frac{\Delta L^*}{K_L S_L}\right)^2 + \left(\frac{\Delta C^*_{ab}}{K_C S_C}\right)^2 + \left(\frac{\Delta H^*_{ab}}{K_H S_H}\right)^2\right]^{0.5} \quad (7)$$

Several alternatives have been developed to solve Equation 7 for obtaining L,C,h values, such as, for example, the well known CIE 94 and CMC equations described below:

| CIE94 Equation | The CMC Equations |
|---|---|
| CR&A, 18, 137-139(1993) For solid colors: $S_L = 1.0$ | For $L* > 16$ $S_L = \frac{0.040975L*}{1 + 0.01765L*}$ |
| For metallic colors: $S_L = 0.034L^*$; If $L^* \leq 29.4$., $S_L = 1.0$ for $L^* \leq 16$ $S_L = 0.511$ | |
| $S_C = 1 + 0.045 C^*_{ab}$ where $C^*_{ab}$ is that of the standard | $S_C = \frac{0.0638 C^*_{ab}}{1 + 0.0131 C^*_{ab}} + 0.638$ |
| $S_H = 1 + 0.015 C^*_{ab}$ | $S_H = (FT + 1 - F) S_C$ where |
| The parametric factors $K_L:K_C:K_H = 1:1:1$ are generally satisfactory. However, if lightness is of lesser importance, $K_L:K_C:K_H$ can be equal to 2:1:1. For metallic color $S_L$ function is provided in Rodrigues A. B. J., Locke, J. S., SPIE Vol. 4421, Editors Robert Chung & Allan Rodrigues, pgs 658-661, which is incorporated herein by reference. | $F = \left[\frac{(C^*_{ab})^4}{(C^*_{ab})^4 + 1900}\right]^{0.5}$ $S_L = \frac{0.040975L*}{1 + 0.01765L*}$ and $T = 0.36 + abs[0.4 \cos(35 + h_{ab})]$ unless h is between 164° and 345° then $T = 0.56 + abs[0.2 \cos(168 + h_{ab})]$ |

It should be noted that even other equations have been developed and continue to be developed for obtaining the L,a,b or L,C,h and ΔE values of color from the measurements of the reflectances of target portion and ΔE for the color difference. The method of the present invention is not bound to any specific equations.

Once the target values of a color of the target portion are determined, step (iii) of the method of the present invention comprises selecting one or more preliminary colorant combinations from a stored list of known colorants in accordance with combinatorial selection criteria to match with said target color values.

There are many ways to create the aforementioned stored list of the colorants. The stored list preferably includes all colorants, such as pigments, dispersions, tints, dyes, metallic flakes (colored aluminum flakes) or a combination thereof that may be needed to produce the matched composition. Each colorant is associated with a database of optical coefficients. Generally, one can produce a matched coating composition by adjusting the concentration in a mixture of several colorants of known optical coefficients that would produce a spectral curve that matches the spectral curve of the target portion. The optical coefficients typically include absorption (K) and scattering (S) coefficients, which can be used in a pigment mixture model (e.g., Kubelka-Munk and others based on radiative transfer theory) to relate pigment mixture concentrations to spectral curve(s) for that mixture.

The well known Kubelka-Munk model relates reflectance at complete hiding to absorption and scattering coefficients for the colorant, typically applied at preset wavelength intervals over the visible spectrum, typically at intervals of 10 nm:

$$K/S = (1-R)^2/2R \quad (8)$$

where K=absorption coefficient, which is an indicator of a coating material's internal absorptance.

S=scattering coefficient, which is the portion of light scattered when traveling through a unit thickness of the coating material; and R=reflectance at complete hiding of the coating material. The reflectance values determined at each wavelength at 10 nanometer intervals of the coating on the target portion are shown in Table 1. The K/S value for a mixture of colorants can be expressed through the following equation:

$$(K/S)_{mix} = (c_1 K_1 + c_2 K_2 + \ldots)/(c_1 S_1 + c_2 S_2 + \ldots) \quad (9)$$

where c=concentration and 1, 2 refer to colorants 1, 2, etc. present in the colorants mixture.

A test coating composition containing a light colorant, such as a white colorant (titanium dioxide pigment) can be typically used to create the database. A test coating composition made from a white colorant was sprayed on a test panel to a dry coating thickness sufficient to completely hide the color of the panel itself, which is typically gray colored. The reflectance of the white coating was then measured at preset wavelength intervals in the visible spectrum, typically at 10 nanometer (nm) intervals starting from 400 nm to 700 nm. Any conventional spectrophotometers, such as that supplied by X-Rite, Grandville, Mich. Model MA100B, MA68II or SP64 can be used to measure the reflectance. Such reflectances, as a function of wavelength, are called the spectral reflectances or spectral curves of that white coating. The measured reflectance, R was substituted into Equation 8 to calculate K/S at each wavelength. It is convenient to assign a value of 1.0 to the scattering coefficients (S) of white colorant at each wavelength. Thus, substituting S=1.0 provides the value for K.

For example, Table 2 below reports reflectances of a white test coating composition measured at wavelengths ranging from 400 nm to 700 nm at 10 nm intervals. The colorant used in the white coating composition was titanium dioxide. In Table 2, the measured reflectance of the white coating at 420 nm is 77.28%. Substituting R=0.7728 into Equation 8 gave K/S=0.0334. Since S=1.0, K would be 0.0334. Similarly, K can be calculated at each wavelength. The results for K/S are reported in the "100% White, K/S" column of Table 2. The separate K and S values for the white are shown in Table 3 later.

A coating composition containing a mixture of 50% black and 50% white was made into paint, sprayed, and its reflectance measured at each wavelength. Another paint that was 100% black was similarly sprayed and measured. The black coating composition was pigmented with carbon black. These measurements are reported in Table 2, along with the corresponding K/S values calculated by Equation 8.

TABLE 2

| Colorant | 100% White | | 100% Black | | 50/50 White/Black | |
|---|---|---|---|---|---|---|
| Nms | R | K/S | R | K/S | R | K/S |
| wl_400 | 0.3404 | 0.6391 | 0.0023 | 220.4118 | 0.2661 | 1.0121 |
| wl_410 | 0.5898 | 0.1426 | 0.0027 | 182.8000 | 0.3795 | 0.5072 |
| wl_420 | 0.7728 | 0.0334 | 0.0031 | 162.1818 | 0.4248 | 0.3893 |
| wl_430 | 0.8327 | 0.0168 | 0.0031 | 159.4091 | 0.4351 | 0.3667 |
| wl_440 | 0.8407 | 0.0151 | 0.0031 | 159.9091 | 0.4354 | 0.3661 |

TABLE 2-continued

| Colorant | 100% White | | 100% Black | | 50/50 White/Black | |
|---|---|---|---|---|---|---|
| Nms | R | K/S | R | K/S | R | K/S |
| wl_450 | 0.8471 | 0.0138 | 0.0031 | 162.0000 | 0.4339 | 0.3694 |
| wl_460 | 0.8534 | 0.0126 | 0.0032 | 156.2174 | 0.4331 | 0.3710 |
| wl_470 | 0.8588 | 0.0116 | 0.0033 | 150.8750 | 0.4323 | 0.3728 |
| wl_480 | 0.8628 | 0.0109 | 0.0033 | 151.7500 | 0.4316 | 0.3742 |
| wl_490 | 0.8670 | 0.0102 | 0.0032 | 152.9583 | 0.4306 | 0.3764 |
| wl_500 | 0.8701 | 0.0097 | 0.0032 | 153.8333 | 0.4299 | 0.3780 |
| wl_510 | 0.8745 | 0.0090 | 0.0033 | 148.6400 | 0.4292 | 0.3797 |
| wl_520 | 0.8785 | 0.0084 | 0.0033 | 149.3200 | 0.4287 | 0.3807 |
| wl_530 | 0.8820 | 0.0079 | 0.0034 | 144.2692 | 0.4281 | 0.3820 |
| wl_540 | 0.8841 | 0.0076 | 0.0034 | 145.5769 | 0.4267 | 0.3851 |
| wl_550 | 0.8855 | 0.0074 | 0.0034 | 146.4615 | 0.4258 | 0.3872 |
| wl_560 | 0.8855 | 0.0074 | 0.0035 | 142.2963 | 0.4243 | 0.3905 |
| wl_570 | 0.8855 | 0.0074 | 0.0035 | 143.3333 | 0.4231 | 0.3933 |
| wl_580 | 0.8862 | 0.0073 | 0.0036 | 139.0000 | 0.4222 | 0.3954 |
| wl_590 | 0.8862 | 0.0073 | 0.0035 | 140.1072 | 0.4209 | 0.3985 |
| wl_600 | 0.8862 | 0.0073 | 0.0036 | 136.1034 | 0.4198 | 0.4008 |
| wl_610 | 0.8855 | 0.0074 | 0.0036 | 136.7931 | 0.4190 | 0.4029 |
| wl_620 | 0.8841 | 0.0076 | 0.0037 | 133.7333 | 0.4170 | 0.4076 |
| wl_630 | 0.8827 | 0.0078 | 0.0037 | 135.2000 | 0.4151 | 0.4122 |
| wl_640 | 0.8813 | 0.0080 | 0.0038 | 132.3226 | 0.4131 | 0.4169 |
| wl_650 | 0.8799 | 0.0082 | 0.0038 | 129.2813 | 0.4116 | 0.4206 |
| wl_660 | 0.8792 | 0.0083 | 0.0039 | 126.6970 | 0.4098 | 0.4250 |
| wl_670 | 0.8778 | 0.0085 | 0.0040 | 124.5000 | 0.4077 | 0.4303 |
| wl_680 | 0.8765 | 0.0087 | 0.0041 | 122.2286 | 0.4058 | 0.4350 |
| wl_690 | 0.8758 | 0.0088 | 0.0042 | 116.7297 | 0.4042 | 0.4391 |
| wl_700 | 0.8758 | 0.0088 | 0.0044 | 111.7949 | 0.4027 | 0.4431 |

For a binary mixture of a colorant plus white, Equation 9 can be written as:

$$(K/S)_{mix} = (c_w K_w + c_c K_c)/(c_w S_w + c_c S_c) \quad (10)$$

At 420 nm, substituting the values of $K_w$ and $S_w$ in Equation (10), $$(K/S)_{mix} = (0.0334 c_w + c_c K_c)/(c_w + c_c S_c)$$

At 420 nm the 50/50 mixture ($c_w = c_c = 0.5$) has R=0.4248 (as shown in Table 2 above), the 100% black has R=0.0031. These are substituted into Equation 8 to provide $(K/S)_{mix}$ with the respective concentrations (50/50 mixture and 100% black). These $(K/S)_{mix}$ values can be then substituted in Equation 8 to provide two equations, which can be simultaneously solved for the two unknowns $K_c$ and $S_c$, providing $K_c=0.3568$ and $S_c=0.0022$. Similarly the K and S of the black can be determined at each wavelength.

The same process allows determination of K and S for each of the colorants used. These are shown in the following Tables 3 and 4, along with K and S values for several other colorants. It should be noted that in practice, several blends of each colorant with white could be used with well known statistical procedures to determine the values of K and S.

TABLE 3

Absorption (K) and Scattering (S) Coefficients for Colorants

| Colorant | White | | Black | | Red Oxide | |
|---|---|---|---|---|---|---|
| data_id | K | S | K | S | K | S |
| wl_400 | 0.6391 | 1.0000 | 0.3747 | 0.0017 | 1.5644 | 0.0226 |
| wl_410 | 0.1426 | 1.0000 | 0.3656 | 0.0020 | 1.5593 | 0.0244 |
| wl_420 | 0.0334 | 1.0000 | 0.3568 | 0.0022 | 1.4739 | 0.0253 |
| wl_430 | 0.0168 | 1.0000 | 0.3507 | 0.0022 | 1.4420 | 0.0263 |
| wl_440 | 0.0151 | 1.0000 | 0.3518 | 0.0022 | 1.4792 | 0.0280 |
| wl_450 | 0.0138 | 1.0000 | 0.3564 | 0.0022 | 1.5006 | 0.0296 |
| wl_460 | 0.0126 | 1.0000 | 0.3593 | 0.0023 | 1.5123 | 0.0313 |
| wl_470 | 0.0116 | 1.0000 | 0.3621 | 0.0024 | 1.5238 | 0.0331 |
| wl_480 | 0.0109 | 1.0000 | 0.3642 | 0.0024 | 1.5338 | 0.0351 |
| wl_490 | 0.0102 | 1.0000 | 0.3671 | 0.0024 | 1.5420 | 0.0378 |
| wl_500 | 0.0097 | 1.0000 | 0.3692 | 0.0024 | 1.5417 | 0.0405 |
| wl_510 | 0.0090 | 1.0000 | 0.3716 | 0.0025 | 1.5365 | 0.0440 |
| wl_520 | 0.0084 | 1.0000 | 0.3733 | 0.0025 | 1.5258 | 0.0484 |
| wl_530 | 0.0079 | 1.0000 | 0.3751 | 0.0026 | 1.4991 | 0.0544 |
| wl_540 | 0.0076 | 1.0000 | 0.3785 | 0.0026 | 1.4393 | 0.0639 |
| wl_550 | 0.0074 | 1.0000 | 0.3808 | 0.0026 | 1.3088 | 0.0797 |
| wl_560 | 0.0074 | 1.0000 | 0.3842 | 0.0027 | 1.0948 | 0.1036 |
| wl_570 | 0.0074 | 1.0000 | 0.3870 | 0.0027 | 0.8291 | 0.1330 |
| wl_580 | 0.0073 | 1.0000 | 0.3892 | 0.0028 | 0.5871 | 0.1594 |
| wl_590 | 0.0073 | 1.0000 | 0.3923 | 0.0028 | 0.4140 | 0.1781 |
| wl_600 | 0.0073 | 1.0000 | 0.3947 | 0.0029 | 0.3057 | 0.1878 |
| wl_610 | 0.0074 | 1.0000 | 0.3967 | 0.0029 | 0.2428 | 0.1916 |
| wl_620 | 0.0076 | 1.0000 | 0.4012 | 0.0030 | 0.2073 | 0.1924 |
| wl_630 | 0.0078 | 1.0000 | 0.4056 | 0.0030 | 0.1858 | 0.1924 |
| wl_640 | 0.0080 | 1.0000 | 0.4102 | 0.0031 | 0.1692 | 0.1909 |
| wl_650 | 0.0082 | 1.0000 | 0.4137 | 0.0032 | 0.1553 | 0.1908 |
| wl_660 | 0.0083 | 1.0000 | 0.4181 | 0.0033 | 0.1418 | 0.1900 |
| wl_670 | 0.0085 | 1.0000 | 0.4233 | 0.0034 | 0.1289 | 0.1900 |
| wl_680 | 0.0087 | 1.0000 | 0.4278 | 0.0035 | 0.1156 | 0.1897 |
| wl_690 | 0.0088 | 1.0000 | 0.4319 | 0.0037 | 0.1028 | 0.1896 |
| wl_700 | 0.0088 | 1.0000 | 0.4360 | 0.0039 | 0.0910 | 0.1887 |

TABLE 4

Absorption (K) and Scattering (S) Coefficients for Colorants

| Colorant | Red 1 | | Yellow | | Red 2 | | Red 3 | |
|---|---|---|---|---|---|---|---|---|
| data_id | K | S | K | S | K | S | K | S |
| wl_400 | 1.3681 | 0.1169 | 3.4994 | 0.0134 | 2.1550 | 0.0084 | 0.5906 | 0.0182 |
| wl_410 | 1.2546 | 0.1105 | 3.7703 | 0.0143 | 2.0614 | 0.0085 | 0.5432 | 0.0168 |
| wl_420 | 1.3386 | 0.0981 | 4.0521 | 0.0182 | 2.7665 | 0.0135 | 0.5245 | 0.0149 |
| wl_430 | 1.5478 | 0.0837 | 4.4643 | 0.0239 | 4.3506 | 0.0261 | 0.5650 | 0.0132 |
| wl_440 | 1.9097 | 0.0698 | 5.0305 | 0.0321 | 6.1708 | 0.0411 | 0.6865 | 0.0122 |
| wl_450 | 2.3670 | 0.0596 | 5.5365 | 0.0409 | 7.9914 | 0.0562 | 0.8568 | 0.0114 |
| wl_460 | 2.8360 | 0.0538 | 6.0349 | 0.0507 | 9.2974 | 0.0687 | 1.0627 | 0.0107 |
| wl_470 | 3.3776 | 0.0506 | 6.4970 | 0.0590 | 10.0134 | 0.0777 | 1.3954 | 0.0104 |
| wl_480 | 4.0108 | 0.0499 | 6.8039 | 0.0617 | 10.0540 | 0.0806 | 1.8751 | 0.0106 |
| wl_490 | 4.4932 | 0.0532 | 7.1009 | 0.0686 | 9.6639 | 0.0794 | 2.3086 | 0.0113 |
| wl_500 | 4.7193 | 0.0538 | 7.4505 | 0.0787 | 9.0982 | 0.0792 | 3.0752 | 0.0133 |
| wl_510 | 5.2135 | 0.0606 | 7.8757 | 0.0887 | 8.0685 | 0.0759 | 4.1112 | 0.0169 |

TABLE 4-continued

Absorption (K) and Scattering (S) Coefficients for Colorants

| Colorant | Red 1 | | Yellow | | Red 2 | | Red 3 | |
|---|---|---|---|---|---|---|---|---|
| data_id | K | S | K | S | K | S | K | S |
| wl_520 | 5.7929 | 0.0722 | 8.0499 | 0.0847 | 7.0089 | 0.0679 | 4.9350 | 0.0203 |
| wl_530 | 6.0009 | 0.0772 | 8.1088 | 0.0801 | 6.2570 | 0.0605 | 5.2736 | 0.0229 |
| wl_540 | 5.9758 | 0.0783 | 8.7268 | 0.1045 | 6.2771 | 0.0578 | 5.0901 | 0.0249 |
| wl_550 | 6.2267 | 0.0877 | 9.7953 | 0.1577 | 6.4474 | 0.0628 | 4.6297 | 0.0273 |
| wl_560 | 6.4646 | 0.1154 | 10.6382 | 0.2081 | 5.6369 | 0.0695 | 3.6371 | 0.0300 |
| wl_570 | 5.6608 | 0.1585 | 10.2559 | 0.2510 | 3.9603 | 0.0726 | 2.3551 | 0.0294 |
| wl_580 | 3.5909 | 0.2118 | 7.1849 | 0.3638 | 2.2508 | 0.0695 | 1.1276 | 0.0262 |
| wl_590 | 1.7339 | 0.2655 | 3.0326 | 0.5296 | 1.1697 | 0.0635 | 0.4224 | 0.0234 |
| wl_600 | 0.6062 | 0.2886 | 0.6601 | 0.5904 | 0.6004 | 0.0581 | 0.1963 | 0.0214 |
| wl_610 | 0.2789 | 0.2813 | 0.2411 | 0.5344 | 0.3244 | 0.0548 | 0.1045 | 0.0198 |
| wl_620 | 0.1574 | 0.2652 | 0.1046 | 0.4752 | 0.1901 | 0.0526 | 0.0679 | 0.0187 |
| wl_630 | 0.1055 | 0.2522 | 0.0526 | 0.4315 | 0.1244 | 0.0510 | 0.0520 | 0.0178 |
| wl_640 | 0.0736 | 0.2427 | 0.0327 | 0.3986 | 0.0921 | 0.0490 | 0.0444 | 0.0170 |
| wl_650 | 0.0560 | 0.2364 | 0.0247 | 0.3752 | 0.0756 | 0.0470 | 0.0403 | 0.0165 |
| wl_660 | 0.0440 | 0.2293 | 0.0204 | 0.3572 | 0.0660 | 0.0449 | 0.0381 | 0.0158 |
| wl_670 | 0.0379 | 0.2231 | 0.0174 | 0.3424 | 0.0594 | 0.0432 | 0.0391 | 0.0154 |
| wl_680 | 0.0341 | 0.2162 | 0.0152 | 0.3302 | 0.0545 | 0.0417 | 0.0446 | 0.0150 |
| wl_690 | 0.0318 | 0.2106 | 0.0138 | 0.3200 | 0.0511 | 0.0403 | 0.0465 | 0.0146 |
| wl_700 | 0.0300 | 0.2038 | 0.0127 | 0.3114 | 0.0488 | 0.0388 | 0.0411 | 0.0145 |

The combinatorial selection criteria on which one or more preliminary colorant combinations from the stored list of known colorants that match with the target color values are selected are for their practicality, i.e., is it practical to make such preliminary combinations? By way of example, assume a case where the colorants used are White (W), Black (B), Red Oxide (RO), Yellow (Y), Red 1 (R1), Red 2 (R2), Red 3 (R3), and it is desired to have a 5-pigment match. It is customary, though not essential to include W and B in each colorant combination attempted. All combinations of the remaining five colorants are taken, three at a time, with W and B to attempt a match. Such a process provides ten possible 5-pigment combinatorial selection criteria:

W, B, RO, Y, R1
W, B, RO, Y, R2
W, B, RO, Y, R3
W, B, RO, R1, R2
W, B, RO, R1, R3
W, B, RO, R2, R3
W, B, Y, R1, R2
W, B, Y, R1, R3
W, B, Y, R2, R3
W, B, R1, R2, R3

By way of example, if a target portion is red, the preliminary combination should not include green, since that combination would result in shading (adjusting) with two complementary colorants. However, red and green together can be used to desaturate and darken the color. The same result can be obtained by using black, which is generally a less expensive colorant. Hence, the normal practice is to avoid shading with complementary colorants.

For solid colors (non-flake) it is preferable to start with 4-colorant combinatorial selection criteria to ascertain whether the resulting color match could be improved with five or six colorants. Preferably, the fewer the number of pigments, the more practical is the resultant preliminary combination, since, a typical refinish body shop would require less time to weigh a 4-colorant automotive paint than a 5- or 6-colorant automotive paint.

Thus, by way of example, from the stored list shown in Tables 2, 3 and 4, the following selected formulas, shown in Table 5 below, would meet the aforedescribed combinatorial selection criteria and also come close to matching the target color values and reflectances. Table 5 reports three preliminary colorant combinations (Formulas 1, 2 and 3) selected on the basis of the combinatorial selection criteria from the stored list that match the target color values and reflectances:

TABLE 5

| Wavelength in nm | Target | Formula 1 | Formula 2 | Formula 3 |
|---|---|---|---|---|
| 400 | 0.0320 | 0.0300 | 0.0260 | 0.0320 |
| 410 | 0.0330 | 0.0310 | 0.0290 | 0.0310 |
| 420 | 0.0290 | 0.0280 | 0.0270 | 0.0250 |
| 430 | 0.0250 | 0.0240 | 0.0250 | 0.0190 |
| 440 | 0.0200 | 0.0200 | 0.0220 | 0.0160 |
| 450 | 0.0160 | 0.0160 | 0.0200 | 0.0130 |
| 460 | 0.0140 | 0.0140 | 0.0180 | 0.0130 |
| 470 | 0.0120 | 0.0120 | 0.0150 | 0.0120 |
| 480 | 0.0110 | 0.0110 | 0.0130 | 0.0120 |
| 490 | 0.0100 | 0.0100 | 0.0120 | 0.0120 |
| 500 | 0.0098 | 0.0100 | 0.0110 | 0.0120 |
| 510 | 0.0098 | 0.0100 | 0.0087 | 0.0130 |
| 520 | 0.0098 | 0.0098 | 0.0076 | 0.0140 |
| 530 | 0.0100 | 0.0100 | 0.0077 | 0.0140 |
| 540 | 0.0100 | 0.0110 | 0.0082 | 0.0140 |
| 550 | 0.0110 | 0.0120 | 0.0087 | 0.0140 |
| 560 | 0.0130 | 0.0140 | 0.0110 | 0.0160 |
| 570 | 0.0180 | 0.0180 | 0.0180 | 0.0210 |
| 580 | 0.0370 | 0.0350 | 0.0390 | 0.0370 |
| 590 | 0.0960 | 0.0940 | 0.1000 | 0.1000 |
| 600 | 0.1880 | 0.1850 | 0.1970 | 0.1880 |
| 610 | 0.2730 | 0.2710 | 0.2760 | 0.2670 |
| 620 | 0.3240 | 0.3240 | 0.3250 | 0.3240 |
| 630 | 0.3500 | 0.3510 | 0.3550 | 0.3570 |
| 640 | 0.3650 | 0.3670 | 0.3700 | 0.3720 |
| 650 | 0.3730 | 0.3770 | 0.3800 | 0.3780 |
| 660 | 0.3790 | 0.3830 | 0.3850 | 0.3800 |
| 670 | 0.3820 | 0.3870 | 0.3810 | 0.3830 |
| 680 | 0.3840 | 0.3890 | 0.3760 | 0.3830 |
| 690 | 0.3860 | 0.3890 | 0.3780 | 0.3810 |
| 700 | 0.3870 | 0.3890 | 0.3830 | 0.3790 |
| L | 30.62 | 30.55 | 30.74 | 31.13 |
| a | 49.87 | 49.78 | 50.77 | 48.2 |
| b | 28.57 | 28.45 | 26.68 | 31.49 |

Figure 2:
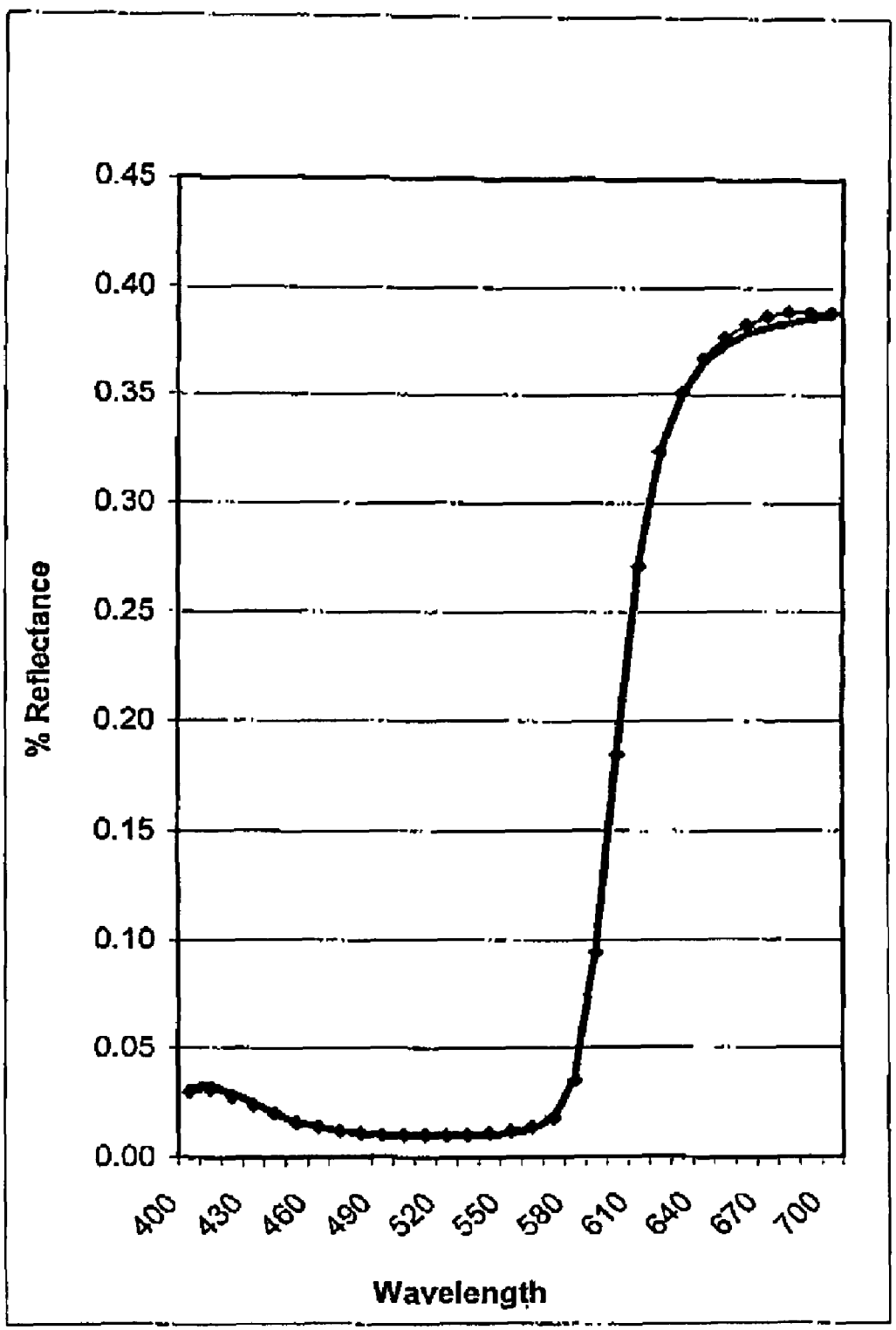
FIG. 2 shows the comparison of the theoretical spectral curves (line with data points) that would result by using the matched coating composition containing the preliminary colorant combinations of Formula 1 with the measured spectral curve from the target portion of the target coating (solid smooth line).
Figure 3:
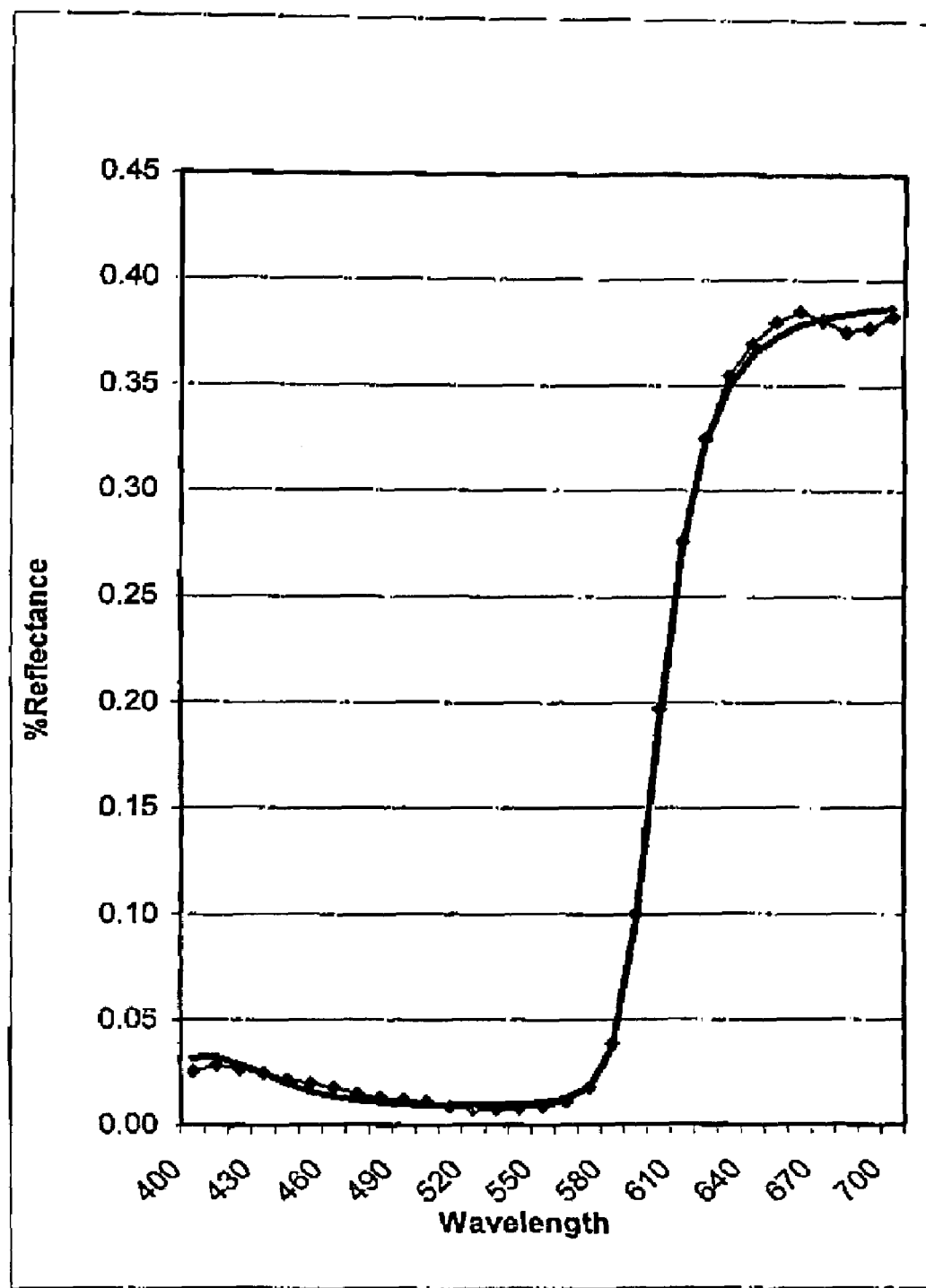
FIG. 3 shows the comparison of the theoretical spectral curves (line with data points) that would result by using the matched coating composition containing the preliminary colorant combinations of Formula 2 with the measured spectral curve from the target portion of the target coating (solid smooth line).
Figure 4:
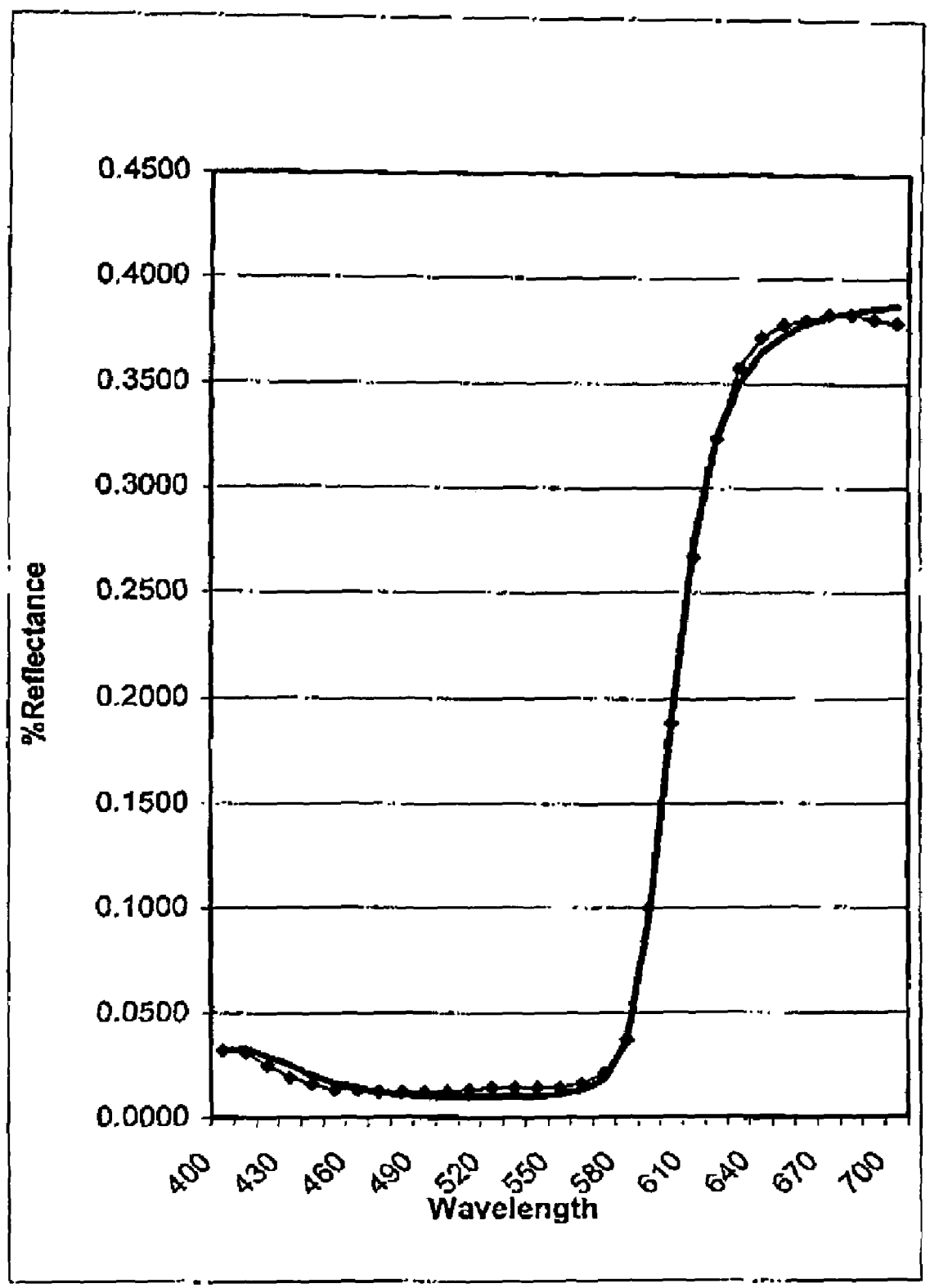
FIG. 4 shows the comparison of the theoretical spectral curves (line with data points) that would result by using the matched coating composition containing the preliminary colorant combinations of Formula 3 with the measured spectral curve from the target portion of the target coating (solid smooth line).

FIGS. 2 through 4 compare the theoretical spectral curves (line with data points) that would result by using the matched coating compositions containing the preliminary colorant combinations of Formula 1 of FIG. 2, Formula 2 of FIG. 3 and Formula 3 of FIG. 4 with the measured spectral curve from the target portion of the target coating (solid smooth line).

Once the preliminary colorant combinations from a stored list of known colorants are selected, in step (iv) of the method of the present invention, concentrations of each of the known colorants in each of the preliminary colorant combinations are determined in accordance with color matching criteria wherein the concentration of each the known colorant is optimized for optimal match of color values of each of the preliminary colorant combinations with the target color values.

The color matching criteria under which the concentrations of each of the known colorants in the preliminary colorant combinations can be obtained are described by E. A. Allen, Basic equations used in computer color matching, *J. Opt. Soc. Am.*, 56, 1256-1259 (1966), which is incorporated herein by reference (hereafter the Allen I reference). It should be noted that the color matching criteria could be configured to eliminate formulas with negative concentrations. In order to make an accurate color match between the target coating with that of a matched coating resulting from the matched coating composition, the concentrations of the colorants in the preliminary colorant combinations should generate spectral curves that would closely match with the spectral curve of the target coating. The foregoing can be accomplished by a simple trial-and-error process, guessing at suitable pigment combinations and concentrations, and by using Equation 9 to calculate the K/S of the mixture at each wavelength. Equation 8 can then be used to convert the K/S of the mixture to its reflectance (R). The resultant spectral curve can be compared to the target spectral curve for a degree of match. If the general shapes of the curves are similar, the right colorants have been chosen. The concentrations then must be adjusted to bring the curves even closer together. The closeness of the spectral curve match could also be judged by calculating the L,a,b values of the match. Such an iterative process can be repeated until the difference in the L,a,b values between the known colorant mixture to the one in the target coating is small. However, such a process would be tedious and time consuming. Moreover, it does it lend itself to automation. The following color matching equation in the aforenoted Allen I reference transformed the color matching equations, allows for a direct solution for concentrations of each known colorant in each of the preliminary colorant combinations by working with a combined K/S ratio rather than separating K and S:

$$\overline{C} = (\overline{TED\Phi})^{-1} \overline{TED} [\overline{f}^{(s)} - \overline{f}^{(t)}] \quad (11)$$

where $\overline{C}$=vector of concentrations of each known colorant in each of the preliminary colorant combinations.

$\overline{T}$=matrix of standard observer weighting functions, which can be obtained from E-308 publication of the American Society of Testing & Materials (ASTM).

$\overline{E}$=vector of relative spectral energy distribution of the light source functions, which can be obtained from ASTM E-308. Illuminant $D_{65}$, representing daylight is commonly used.

$\overline{D}$=matrix of dR/d(K/S) functions obtained by calculating the partial derivative of Equation 8 yielding dR/d(K/S)=$-2R^2/(1-R^2)$.

$\overline{\Phi}$=matrix of K/S values for all colorants in each of the preliminary colorant combinations.

$\overline{f}^{(t)}$=vector of K/S for target portion (t).

$\overline{f}^{(1)}$=vector of K/S for underlying substrate in case of dye mixtures or that of white colorant for pastel shade coating compositions.

Equation 11 works well for dye mixtures on substrates; such as textiles because dyes typically have high absorption coefficients (K) but low scattering coefficients (S) while the substrate on which the dyes are applied typically has high scattering coefficients (S) but low absorption coefficients (K), i.e., Equation 11 would be valid for pastel shade paints with large amounts of highly scattering titanium dioxide pigment and much lower quantities of strongly absorbing pigments.

The concentrations provided by Equation 11 are useful when the colorant combination chosen allows for a non-metameric match. When the colorant combination chosen allows only a metameric match, the concentrations provided by Equation 11 can be iteratively adjusted to a metameric match acceptably low in color difference from the target color. However, yet another approach can be used for non-pastel color, which is reported in E. A. Allen in Basic Equations used in computer color matching, II. Tristmulus matching, two-constant theory, J. Opt. Soc. Am. 64, 991-993 (1974), (hereafter Allen II reference).

Still another approach was provided by Rodrigues (7th *Congress of the International Colour Association (AIC), Budapest*, June 1993 (hereafter the Rodrigues reference) though the following matrix equation:

$$\overline{C} = (\overline{TED\psi})^{-1} \overline{TED\theta}_1 \quad (12)$$

where
$\psi_j = K_j - K_1 - \theta_s(S_j - S_1)$ for each wavelength,
$\theta_t = (K/S)_t$, and
$\theta_1 = \psi_j$ where $K_j = S_j = 0$.

Subscript j refers to colorant j in a group of colorants in the preliminary colorant combinations and 1 refers to colorant 1 in the preliminary colorant combinations and subscript t refers to the target coating.

When the colorants chosen allow for a non-metameric match, Equation 12 provides for concentrations for a close color match. However, similar to Equation 11, Equation 12 provides for only an approximate match when the colorants chosen allow for only a metameric match. To improve the match in Equation 12, the concentrations of colorants in the matched composition can be iteratively adjusted to provide for an acceptable match by using the following matrix equation:

$$\overline{\Delta C} = (\overline{TED\psi'})^{-1} \overline{\Delta t} \quad (13)$$

where,
$\psi'_j = \psi_j / \Sigma S_j C_j$ and wherein the summation includes all the colorants in each of the preliminary colorant combinations,
$\overline{\Delta C}$ is the vector of concentration adjustments to C matrix of Equation 12, and
$\overline{\Delta t}$ is the vector of tristimulus color differences between the target coating and the approximate match of concentration C given by Equation 12.

The concentration adjustments from Equation 13 are applied to the concentrations from Equation 12. These new concentrations are then substituted in Equation 9 to calculate new $(K/S)_{mix}$ at each wavelength, which in turn are used in Equation 8 to generate a new spectral curve. Color differences between the new spectral curve and that of the target are calculated by using the aforedescribed Equation A. This process is repeated iteratively until the color differences are acceptably small for the specified end use.

The color matching criteria described above allows a computer program to choose various preliminary colorant combinations and get the theoretical concentration for each colorant in each of those preliminary colorant combinations. It is possible that the solution of Equations 12 and 13 could provide negative concentrations. For example, if a blue pigment was included in attempting to match the yellow-shade red example shown above, the only way it could be matched would be to use a negative amount of blue (complement of yellow), which would be physically impossible and thus the color matching criteria can be configured to automatically eliminate such combinations. The theoretical concentrations of colorants in the preliminary colorant combinations in Formulas 1, 2 and 3 as determined though the color matching criteria expressed in Equations 12 and 13 are shown in Table 6 below:

TABLE 6

| Colorants | Colorant Concentrations | | |
|---|---|---|---|
| | Formula 1 | Formula 2 | Formula 3 |
| White | 0.52 | 0.34 | 0.34 |
| Black | 1.61 | 0.16 | 0.42 |
| Red Oxide | 2.75 | 1.38 | |
| Red1 | 7.23 | | |
| Yellow | 1.79 | 1.12 | 0.9 |
| Red2 | | 4.18 | |
| Red3 | | | 1.47 |

Metallic colors can be also matched through similar processes. The absorption and scattering coefficients for colorants are then generally determined relative to aluminum flake dispersion instead of white. The K and S values for each pigment must be determined separately at each of the angles of measurement. A problem can arise at low aspecular angles (e.g., 15 or 25 degrees) where reflectances (R) may exceed 1.0 for very light colors, making Equation 8 ambiguous because of the squared term, i.e., the same value of K/S can be obtained for two different values of R. Values of R greater than 1.0 are possible because the reflectance (referred to as reflectance factor in ASTM E-284) is determined as the reflectance of the color sample at a particular angle of measurement as compared to that of the perfect diffuser at that same measurement condition. Pressed barium sulfate is a good approximation of a perfect diffuser. At these near-specular angles, bright aluminum flakes can exceed the lightness of the perfect diffuser measured at that same angle. One of the ways of determining concentrations in the preliminary colorant combination that includes metallic flakes is provided in claim 8 and also at Column 9, line 55-column 10, line 61 and column 18, line 9-column 28, line 5 in the U.S. Pat. No. 5,231,472. Yet another model for gonioapparent colors is discussed in Kettler, W. H., Kolb, M., "Numerical evaluation of optical single-scattering properties of reflective pigments using multiple-scattering inverse transport methods", Die Farbe, Vol. 43, pg. 167 (1997) and Kettler, W. H., Kolb, M., "Inverse multiple scattering calculations for plane-parallel turbid media: application to color recipe formulation", in Proceedings of the International Workshop, Electromagnetic Light Scattering, Theory and Application, Lomonosov State University, Moscow, Edited by Y. Eremin and Th. Wriedt (1997). All of the foregoing references are incorporated herein by reference.

Since, the matched compositions need to be balanced to achieve the desired film properties, step (v) of the method of the present invention includes balancing the preliminary colorant combinations to allow for the presence of non-colorant components, such as binder polymers or solvents, in the matched coating composition to generate one or more viable combinations optimized in accordance with mixing and regulatory criteria developed for the specified end-use.

It is well understood in the coating art to balance the various components in a coating compositions based on the specific end use that is desired. For example, the durability requirement of a coating in an interior application, such as wall coatings applied over interior walls of a house would be less important than the durability requirements of outdoor coatings applied to exterior walls of a house that get exposed to UV radiation from the sun light. Similarly, the coating properties requirements for coating compositions used in disparate geographic locations, such as those used in cold and wet climates, such as in Canada would be far different than the those used in hot and arid climates, such as in Saharan desert. By way another example, the adhesion properties of coatings used in automotive applications would be different than those coatings used on coating home appliances. Those skilled in the coating arts empirically develop their own mixing and regulatory criteria tailored for a specified end-use.

Thus, the presence of other non-colorant components is necessary to provide the resulting coating composition with application properties and good coating properties, such as adhesion, gloss, and durability, when a layer of the coating composition applied over a substrate surface cures into a coating. A non-colorant component, such as a solvent, is typically included in a coating composition to improve its application properties that result in an even flow out after spraying, without an "orange peel" surface or sagging on a vertical surface.

Thus, too little film build can adversely affect the hiding obtained by the coating and too much film build can result in sagging of the paint layer as it dries into a coating. Car refinishers also prefer automotive paints to cover the substrate in two coats since a single coat hiding can result in a splotchy appearance. However, application of more than two coats increases the labor cost and paint cost required to repair the car and is thus undesirable.

Other non-colorant components, such as binder polymers, are also included in the coating composition to improve, for example, the adhesion of the resulting coating to the underlying substrate. It is also desirable to balance the non-colorant components, such as solvent, in the coating composition, to meet regulatory requirements such as, for example, lowering the volatile organic content (VOC) of the coating composition. Other non-colorant components used include additives, such as UV screeners, hindered amine light stabilizers for improving durability, rheology control agents, flow agents, adhesion promoters, catalysts and anti-crater agents. Yet another example of a common requirement would be to control the solids of a coating composition. Coating solids level affects such properties as the rate of film build, rheology, VOC and cost of the coating composition. Typically, solids are restricted to a narrower range, such as for example, coating solids for a high solids refinish coating compositions being at about 60%±1%.

Percent solids for the coating can be expressed by the following formula:

$$100*(\Sigma SW_i/\Sigma TW_i) \quad (14)$$

where the solids weight of each component $SW_1$ to $SW_i$ in a coating composition is summed up and then divided by the sum of the total weight of each individual component $TW_1$ to $TW_i$, i.e., (includes a solid part and a liquid part, if used, of each individual component).

One skilled in the art would recognize that the solids weight (SW), as used in the current context, includes all components that form part of the resultant coating, even though in the coating composition they may have been in a liquid form. For example, crosslinkers, which are often, low in the molecular weight and can be present, as liquid in the coating composition then become part of the coating structure when the crosslinkers in the coating composition crosslink after application. Thus, the desired solids requirement (the amount solvent used and/or amount and type of binder polymers used), such as those for low solids or high solids matched coating composition, can be obtained by using the aforementioned Equation 14.

It may be necessary for the matched coating composition to meet environmental regulatory requirements, such as limiting the VOC of the match coating composition as promulgated from time to time by the various government agencies, such as the Environmental Protection Agency of the United States. One of the limits typically specified through various statutes and regulations is to limit the weight of a solvent included in a specified volume of coating composition. The VOC is normally expressed as kilograms of solvent per liter of coating composition, or in the United States it can be expressed as pounds of solvent per gallon of a coating composition. Such a limitation can vary in accordance with the intended use. The aforedescribed VOC limitation can be expressed by the following formula:

$$\Sigma S_i/V \tag{15}$$

where the weight of the solvent in kilograms for each component $S_1$ to $S_i$ is summed and divided by the volume of the final coating composition expressed in liters. Thus, it is readily apparent that even other requirements for the matched coating composition could be programmed by using suitably developed formulas to balance the color formula based on the types and amounts non-colorant components required to meet the requirement for a specified end use.

Table 7 below shows the results of the foregoing balancing step used for optimizing the preliminary colorant combinations into the viable colorant combinations (Formulas* 1, 2 and 3) by including the amount of the balancing component needed to meet the mixing and regulatory criteria for a specified end use.

TABLE 7

| Colorants | Colorant Concentrations | | |
|---|---|---|---|
| | Formula* 1 | Formula* 2 | Formula* 3 |
| White | 0.52 | 0.34 | 0.34 |
| Black | 1.61 | 0.16 | 0.42 |
| Red Oxide | 2.75 | 1.38 | |
| Red1 | 7.23 | | |
| Yellow | 1.79 | 1.12 | 0.9 |
| Red2 | | 4.18 | |
| Red3 | | | 1.47 |
| Balancing Component | 86.1 | 92.81 | 96.86 |
| Total | 100 | 100 | 100 |

Step (vi) of the present method comprises selecting an optimal viable combination from the viable colorant combinations (Formulas* 1, 2, and 3 in Table 7 above) in accordance with an acceptability equation for the specified end-use, the optimal viable combination having an optimal acceptability value for the specified end-use wherein the known colorants and non-colorant components when mixed in accordance with the optimal. viable combination produce the matched coating composition that when applied as a matched coating visually matches with the appearance of the target coating.

The aforementioned acceptability equation for a specified end use is expressed as:

$$\text{Acceptability value} = \Sigma \text{Acceptability factor}_i * \text{weight}_i \tag{16}$$

Depending on the specified end use, a weight can be empirically developed for each of the following acceptability factors used in calculating the acceptability value. The summation of the acceptability factors multiplied by the weight assigned to each such factor results in the acceptability value of the matched composition in accordance with the aforementioned Equation 16. The lower the acceptability value for the specified end use, the more optimal would be viable combination.

Several of the following acceptability factors can be calculated for each viable colorant combination:

1. Color difference: This factor relates to the degree of color difference between the target coating and a matched coating obtained from a coating composition formulated in accordance with each of the viable colorant combinations (Formulas* 1, 2 and 3). Several color difference equations published in the literature can be used. The International Committee on Illumination (CIE) in 1994 recommended a color difference metric now referred to as the aforedescribed "CIE94 Equations" or the "CMC Equations". These equations provide a mathematical estimate of the accuracy of color match that would be observed by a normal observer under a given lighting condition, typically using the D65 illuminant, representing average daylight.

2. Metamerism: A match may appear acceptable under one illuminant but not another or when viewed by different observers. Metamerism Indices calculate color differences under two different illuminants (usually D65 and A, which can be a common incandescent or fluorescent light). The vector difference between these two color differences is calculated as an indicator of metamerism. The following equations can be used to determine the metamerism:

The Tannenbaum Metamerism Index can be determined by the following equations:

$$G_0 = -0.4632X_0 + 1.3677Y_0 + 0.0955Z_0 \tag{17}$$

$$B_0 = -0.4632X_0 + 1.3677Y_0 + 0.0955Z_0 \tag{18}$$

$$R_0 = 0.7584X_0 + 0.3980Y_0 - 0.1564Z_0 \tag{19}$$

Where $X_0$, $Y_0$, and $Z_0$ are the X, Y and Z of the illuminant.

$$R = (0.7584X + 0.3980Y - 0.1564Z)*100/G_0 \tag{18}$$

$$G = (-0.4632X + 1.3677Y + 0.0955Z)*100/G_0 \tag{19}$$

$$B = (-0.1220X + 0.3605Y + 0.7615Z)*100/G_0 \tag{20}$$

$$L = 25G^{1/3} - 16 \tag{21}$$

$$a = a' - (Y/100)^{1/3}a_0 \tag{22}$$

$$b = b' - (Y/100)^{1/3}b_0 \tag{23}$$

where $$a' = 500[(R/100)^{1/3} - (G/100)^{1/3}] \tag{24}$$

$$b' = 200[(G/100)^{1/3} - (B/100)^{1/3}] \tag{25}$$

$a_0$, $b_0$ are calculated from these equations by using $R_0$, $G_0$, $B_0$ and therefore Metamerism index MI is provided by:

$$MI = \sqrt{(\Delta L_C - \Delta L_A)^2 + (\Delta a_C - \Delta a_A)^2 + (\Delta b_C - \Delta b_A)^2} \tag{26}$$

The lower the metamerism (MI), the better would be the color match under various lighting conditions.

3. Closeness of spectral curve match: When the same pigmentation and concentrations are used in the target and matched coatings, their spectral curves would be identical. This would be the ideal match in terms of color accuracy. Thus an indicator of closeness of spectral curve match is also a useful index; An example of this acceptability factor sometimes referred to as the Reilly Metamerism Potential is shown below. Other measures of closeness of spectral curve match that are also suitable are provided by Nimeroff, I., and Yurow, J. A., in "Degree of Metamerism", J. Opt. Soc. Am., Volume 55, 185-190 (1965), which is incorporated herein by reference.

Reilly Metamerism Potential is obtained by the following equation:

$$\text{Metamerism Potential} = \sqrt{K_L^2\left(\frac{\Delta G}{G_0^{2/3}}\right)^2 + K_a^2\left(\frac{\Delta R}{R_0^{2/3}} - \frac{\Delta G}{G_0^{2/3}}\right)^2 + K_b^2\left(\frac{\Delta G}{G_0^{2/3}} - \frac{\Delta B}{B_0^{2/3}}\right)^2} \quad (27)$$

where $\Delta R = \Sigma |A_r \cdot \rho_{b\lambda} - \rho_{s\lambda}| \cdot \bar{r}_\lambda$, $\Delta G = \Sigma |A_g \cdot \rho_{b\lambda} - \rho_{s\lambda}| \cdot \bar{g}_\lambda$, and $\Delta B = \Sigma |A_b \cdot \rho_{b\lambda} - \rho_{s\lambda}| \cdot \bar{b}_\lambda$;

and $A_r = R_0/R_b, A_g = G_0/G_b, A_b = B_0/B_b$, $R = X/X_0, G = Y/Y_0, B = Z/Z_0$;

$\bar{r}_{80} = \bar{x}_\lambda/X_0, \bar{g}_\lambda = \bar{y}_\lambda/Y_0, \bar{b}_\lambda = \bar{z}_\lambda/Z_0$;

$\bar{x}_\lambda, \bar{y}_\lambda, \bar{z}_\lambda$ being the tristimulus observer weighting functions; and X, Y, and Z being the tristimulus values of target or matched coating.

In the foregoing, the subscript "0" refers to the corresponding X, Y, and Z for the illuminant.

$K_L$ 25.00, $K_a$ 107.72 and $K_b$ is 43.09, which are the CIELAB coordinate scaling factors.

$\rho_\lambda$=spectral reflectance at wavelength $\lambda$, subscript s refers to the target coating and b refers to the matched coating, and R ($X/X_0$), G ($Y/Y_0$), B ($Z/Z_0$) are preferably computed for the standard observer and the equal energy spectrum.

4. Durability: Depending on its end-use, this acceptability factor of a coating composition can be an important factor. Some colorants are more durable than others. Each colorant can be assigned a "durability indicator" based on empirical durability tests, such as Florida exposure studies. The sum of the concentration-weighted indicators of each colorant in the viable colorant combination can be used as a durability index of that formula.

5. Cost: Depending on its end-use, this acceptability factor may or may not be an important factor. For example, in automotive refinish applications, durability and accuracy of color match far outweigh the cost of the coating composition. Moreover, the cost of the coating composition is less significant when compared to the labor costs incurred in repairing an autobody. Since inaccurate color match increases the labor cost in completing the autobody repair and poor durability of auto paint can result in warrantee complaints, these factor far outweigh the paint costs. In view of the foregoing, the cost the resultant coating compositions in automotive refinish application will be assigned substantially less weight as compared to the other factors, such as durability and accuracy of color match. By contrast, with interior wall paints however, the paint is generally not exposed to strong sunlight or corrosive atmospheres, so the durability factor is less important. Accuracy of color match is also not of great concern as long as the color consistency is maintained from batch-to-batch. Cost however is an important factor for wall paints. Costs of ingredients and ingredient densities can be stored in the database of the computer used by the characterizing device of the present invention to compute the cost per unit volume of paint from the formula.

For example, an automotive customer usually requires a good match, regardless of cost, while durability is also important. Hence color difference may be assigned a weight of 30, closeness of curve match a weight of 30, metamerism a weight of 25, durability a weight of 15 and cost a weight equal to zero.

The foregoing provides acceptability values of 46.5 for Formula* 1, 193.6 for Formula* 2, 257.5 for Formula 3; clearly indicating that Formula* 1 should be used in case of automotive refinish application.

Table 8 shows possible weighting factors for cases where low cost is important (resulting in the choice of Formula* 3; and where high durability is most important, resulting in the choice of Formula* 2. These weights may be tailored to a particular customer or particular end use for the coating composition.

Note that for gonioapparent colors the color differences, metamerism, and closeness of spectral match should be calculated at multiple angles (preferably 3 to 5) and then combined. Angles can be weighted in accordance with the user or customer preference, if known.

TABLE 8

Calculation of Durability and Cost Indices

| | | Formula* 1 | | Formula* 2 | | Formula* 3 | |
|---|---|---|---|---|---|---|---|
| | D.I. | C. | A.F. | C | A.F. | C | A.F. |
| White | 0 | 0.52 | 0 | 0.34 | 0 | 0.34 | 0 |
| Black | 0 | 1.61 | 0 | 0.16 | 0 | 0.42 | 0 |
| Red Oxide | 0 | 2.75 | 0 | 1.38 | 0 | | 0 |
| Red1 | 2 | 7.23 | 14.46 | | 0 | | 0 |
| Yellow | 1 | 1.79 | 1.79 | 1.12 | 1.12 | 0.9 | 0.9 |
| Red2 | 1 | | 0 | 4.18 | 4.18 | | 0 |
| Red3 | 2 | | 0 | | 0 | 1.47 | 2.94 |
| B.C. | | 86.1 | | 92.81 | | 96.86 | |
| Total | | 100 | 16.25 | 100 | 5.3 | 100 | 3.84 |
| Total, (colorants weights only) | | 13.9 | | 7.18 | | 3.13 | |
| Durability Index | | | 1.17 | | 0.74 | | 1.23 |
| Cost per 0.2 liters | | $3.61 | | $2.90 | | $2.42 | |

Notes:
1. D.I. means durability indicator.
2. C. means Concentration.
3. A.F. means acceptability factor.
4. B.C. means balancing components, such as solvent and binder polymers.
5. The concentration of each ingredient is multiplied by its durability indicator to arrive at the acceptability factor for that ingredient.
6. These acceptability factors are totaled and then divided by the total weight of the colorants to provide the durability index of that formula.
7. The cost in US dollars per 0.2 liters is used so as to keep its magnitude in line with other factors.

TABLE 9

| Factors | Formula* 1 | Formula* 2 | Formula* 3 | Weights for Closer match | Weights for Lower cost | Weights for Higher durability |
|---|---|---|---|---|---|---|
| CIE94 ΔE | 0.08 | 1.13 | 1.89 | 30 | 10 | 10 |
| Reilly Potential | 0.67 | 4.32 | 4.82 | 30 | 0 | 0 |
| T.M.I. | 0.26 | 0.76 | 1.51 | 25 | 5 | 10 |
| Durability | 1.17 | 0.74 | 1.23 | 15 | 5 | 80 |
| Cost/.02 lit | 3.61 | 2.90 | 2.42 | 0 | 80 | 0 |
| Totals | | | | 100 | 100 | 100 |

T.M.I. means Tannenbaum metamerism index

TABLE 10

| | Calculated Acceptability Values | | | | | | | | |
|---|---|---|---|---|---|---|---|---|---|
| | Degree of match between target and matched coatings from Formulas | | | Cost of coating composition from Formulas | | | Durability of matched coating from Formulas | | |
| Factors | Rx 1 | Rx 2 | Rx 3 | Rx 1 | Rx 2 | Rx 3 | Rx 1 | Rx 2 | Rx 3 |
| CIE94 ΔE | 2.4 | 33.9 | 56.7 | 0.8 | 11.3 | 18.9 | 0.8 | 11.3 | 18.9 |
| Reilly Potential | 20.1 | 129.6 | 144.6 | 0 | 0 | 0 | 0 | 0 | 0 |
| T.M.I. | 6.5 | 19 | 37.75 | 1.3 | 3.8 | 7.55 | 2.6 | 7.6 | 15.1 |
| Durability | 17.5 | 11.1 | 18.4 | 5.8 | 3.7 | 6.1 | 93.5 | 59.1 | 98.1 |
| Cost/.02 liter | 0.0 | 0.0 | 0.0 | 288.7 | 232.1 | 194.0 | 0.0 | 0.0 | 0.0 |
| Totals | 46.5 | 193.6 | 257.5 | 296.7 | 250.9 | 226.5 | 96.9 | 78.0 | 132.1 |

Rx means Formula*.

Example of calculating the acceptability value:

Formula* 1 was found to have a CIE94 ΔE=0.08, as reported in Table 9. The weight assigned for the "best match" formula was 30. Hence the CIE94 ΔE acceptability was 0.08× 30=2.4 (reported in Table 10). Similarly the Reilly Potential acceptability was 0.67×30=20.1. PMT Index acceptability was 0.26×25=6.5. Durability acceptability was 1.17×15=17.5 (reported in Table 10). Cost/0.02 liter acceptability was 3.61×0=0 (reported in Table 10). The summation of weight times the acceptability factor total up to the acceptability value of Formula* 1 at 46.5.

As reported in Table 10, Formulas* 2 and 3 can be similarly reported. Since the acceptability value for color match for Formula I is the lowest, it would be chosen as the best formula when the criterion for acceptability is color match rather than cost or durability.

Similar calculations show that Formula* 3 as being the best when cost is more important and Formula* 2 as being the best when durability is more important.

The method of the present invention further comprises displaying on a screen of a monitor of the device the optimal viable combination, which has the best acceptability value, i.e., the lowest acceptability value for the specified end use.

The method of the present invention also comprises mixing the components, such as colorants, solvents, binder polymers, and additives listed in the optimal viable combination using conventional mixers to produce the matched coating composition.

The method of the present invention also comprises applying the matched coating composition over a substrate, such as automotive body, by conventional application methods, such as spraying, roller coating, or dip coating, to produce the matched coating that visually matches with the appearance of the target coating.

The matched coating composition produced or obtained in accordance with the method of the present invention can be an OEM automotive paint, refinish automotive paint, architectural paint, industrial coating composition, powder coating composition, printing ink, ink jet ink, nail polish, food colorant, eye shadow, or hair dye.

Another embodiment of the method of present invention comprises producing a matched resin, such as those processed in injection molding, blow molding, rotational molding, thermoforming or extruding into a specified end-use, such as dashboard, interior door panels or bumper guard of an automobile; or consumer products. The process can provide the formulator with an optimal viable combination for said specified end-use, such as that components in the optimal viable combination when mixed produce a matched resin that when formed as a matched substrate visually matches with the appearance of a target substrate, such as automobile upholstery or autobody.

The foregoing method can further comprise:

(a) mixing the components in the optimal viable combination with a resin to produce the matched resin; and (b) processing the matched resin into the matched substrate.

The foregoing mixing step can be conventionally accomplished by melting and extruding the components through a conventional extruder into the matched resin and then converting it in a powder or pelletized form.

The present Invention is also directed to a color characterizing device 1 shown in FIG. 1 for producing a matched coating composition for a specified end-use. Device 1 comprises:

(i) a spectrophotometer 2 of device 1, such as a conventional multi-angle spectrophotometer or sphere geometry spectrophotometer, having a base for positioning spectrophotometer 2 over a target portion of a target coating;

(ii) means for calculating target color (L,a,b or L,C,h) values of the target portion;

(iii) a computer usable storage medium 4 located in a computer 6 of device 1 having computer readable program code means residing therein, the computer readable program code means comprising:

(a) means for configuring computer readable program code devices to cause computer 6 to select one or more preliminary colorant combinations from a stored list of known colorants in accordance with a combinatorial selection criteria to match with the target color space values;

(b) means for configuring computer readable program code devices to cause computer 6 to determine concentration of each the known colorant in each of the preliminary colorant combinations in accordance with color matching criteria wherein the concentration of each the known colorant is optimized for optimal match of color values of each of the preliminary colorant combinations with the target color values;

(d) means for configuring computer readable program code devices to cause computer 6 to balance the preliminary colorant combinations to allow for the presence of non-colorant components in the matched coating composition to generate one or more viable combinations optimized in accordance with mixing and regulatory criteria developed for the specified end-use; and (e) means for configuring computer readable program code devices to cause computer 6 to select an optimal viable combination from the viable combinations in accordance with an acceptabiiity equation for the specified end-use, the optimal viable combination having an optimal acceptability value for the specified end-use wherein the known colorants and non-colorant components when mixed in accordance with the optimal viable combination produce the matched coating composition that when applied as a matched coating visually matches with the appearance of the target coating.

Device 1 further comprises means for configuring computer readable program code devices to cause computer 6 to display on a screen of a monitor 8 of device 1 the optimal viable combination.

Device 1 can further comprise:

(a) means for configuring computer readable program code devices to cause computer 6 to generate a signal in accordance with the optimal viable combination to dispense the components for making a desired amount of the matched coating composition;

(b) a dispenser 10 for dispensing the components in a container 12, dispenser 10 being in communication with computer 6:

(c) means for configuring computer readable program code devices to cause computer 6 to generate a signal upon completion of making the desired amount of the matched coating composition; and (d) means for configuring computer readable program code devices to cause computer 6 to generate a signal to dispenser 10 to stop dispensing of the components.

Device 1 can further comprise a mixer, not shown in FIG. 1, for mixing the components dispensed in container 12.

Device 1 of the present invention is a preferably transportable device to permit ready positioning of spectrophotometer 2 of device 1 on substrate of various shapes, such as automotive body.

Generally, the computer readable program code means of the present invention can be stored on a conventional portable computer usable storage medium, such as a CD-Rom and the computer readable program code can be programmed by using conventional programming software, such as C++Builder, Version 5 or Delphi, Version 6, both supplied by Borland Corporation located in Scotts Valley, Calif.

Computer 6 suitable for use in the present invention can be any conventional computer/processor such as those supplied by Dell Computer Corporation. Round Rock, Tex. or IBM Corporation, Armonk, N.Y. that can be configured to execute conventional computer program codes. For example, Model No. Dimension™4100 supplied by Dell Computer Corporation utilizing Windows® XP operating system supplied by Microsoft Corporation located in Redmond, Wash. can be utilized.

The present method is equally well suited for using a computer set up wherein computer 6 of device 1 is in communication with a host computer, not shown. It would be understood that the communication between the host computer and computer 6 of device 1 can be through a modem or via a website. Moreover, the database of the stored list of known colorants can reside either on a storage device of computer 6 of device 1 or on a storage device of the host computer. It should be understood that computer 6 of device 1 and the host computer can be located anywhere, such as for example computer 6 of device 1 can be located in one country, such as the United States, or another state and the host computer can be located in another country, such as Canada, or another state. Alternatively, the host computer can be located In one county, such as United States, or another state and computer 6 of device 1 can be located in another country, such as Canada, or another state. It should be further understood that the host computer could be in communication with plurality of computers 6 of devices 1 being used.

What is claimed is:

1. A method for producing a matched coating composition for a specified end-use, said method comprising:

(i) measuring reflectances of a target portion of a target coating at a set of preset wavelengths with a spectrophotometer of a coating characterizing device to plot a target spectral curve of said target portion, wherein said target coating is on an undamaged portion of an auto body, plastic substrate, marine substrate, and aluminum substrate;

(ii) calculating target color (L,a,b or L,C,h) values of said target portion from said target spectral curve of said target portion;

(iii) selecting one or more preliminary colorant combinations from a stored list of known colorants in accordance with a combinatorial selection criteria to match with said target color values, wherein said stored list of known colorants comprises pigments, dispersions, tints, dyes, metallic flakes or a combination thereof, and wherein said combinatorial selection criteria comprise avoiding shading with complementary colorants and preferring colorant combinations with a fewer number of pigments than a greater number of pigments;

(iv) determining concentration of each said known colorant in each of said preliminary colorant combinations in accordance with color matching criteria wherein said concentration of each said known colorant is optimized for optimal match of color values of each of said preliminary colorant combinations with said target color values;

(v) balancing said preliminary colorant combinations to allow for presence of non-colorant components in said matched coating composition to generate one or more viable combinations optimized in accordance with mixing and regulatory criteria developed for said specified end-use;

(vi) selecting an optimal viable combination from said viable combinations in accordance with an acceptability equation for said specified end-use, said optimal viable combination having an optimal acceptability value for said specified end-use wherein said known colorants and non-colorant components when mixed in accordance with said optimal viable combination produce said matched coating composition that when applied as a matched coating visually matches with appearance of said target coating, wherein said acceptability equation is a summation of acceptability factors multiplied by a weight assigned to each said acceptability factor, wherein said acceptability factors comprise color difference, metamerism, closeness of spectral curve match, durability or cost; and (vii) displaying on a screen of a monitor of said device said optimal viable combination.

2. The method of claim 1 further comprising mixing said components of said optimal viable combination to produce said matched coating composition.

3. The method of claim 1 wherein said matched coating composition is an OEM automotive paint, refinish automotive paint architectural paint, industrial coating composition, powder coating composition, printing ink, ink jet ink, nail polish, food colorant, eye shadow, or hair dye.

4. The method of claim 1 wherein each of said preliminary colorant combinations comprises one to seven said known colorants.

5. The method of claim 1 wherein said step (ii) comprises:
(a) directing a beam of light of a known intensity towards said target portion; and
(b) sequentially measuring at at least one aspecular angle said reflectances of said target portion at said set of preset wavelengths.

6. The method of claim 1 wherein said step (ii) comprises:
(a) sequentially directing one or more beams of light of a known intensity at at least one incident angle towards said target portion; and
(b) sequentially measuring at an aspecular angle said reflectances of said target portion at said set of preset wavelengths.

7. The method of claim 1 further comprising applying said matched coating composition over a substrate to produce said coating that visually matches the appearance of said target coating.

8. The method of claim 7 wherein said substrate is an automotive body.

9. A matched coating composition produced by the method of claim 1.

10. A color characterizing device for producing a matched coating composition for a specified end-use, said device comprising:
(i) a spectrophotometer of said device having a base for positioning said spectrophotometer over a target portion of a target coating, wherein said target coating is on an undamaged portion of an auto body, plastic substrate, marine substrate, and aluminum substrate;
(ii) means for calculating target color (L,a,b or L,C,h) values of said target portion;
(iii) a computer usable storage medium located in a computer of said device having computer readable program code means residing therein, said computer readable program code means comprising:
(a) means for configuring computer readable program code devices to cause said computer to select one or more preliminary colorant combinations from a stored list of known colorants in accordance with a combinatorial selection criteria to match with said target color values, wherein said stored list of known colorants comprises pigments, dispersions, tints, dyes, metallic flakes or a combination thereof, and wherein said combinatorial selection criteria comprise avoiding shading with complementary colorants and preferring colorant combinations with a fewer number of pigments than a greater number of pigments;
(b) means for configuring computer readable program code devices to cause said computer to determine concentration of each said known colorant in each of said preliminary colorant combinations in accordance with color matching criteria wherein said concentration of each said known colorant is optimized for optimal match of color values of each of said preliminary colorant combinations with said target color values;
(c) means for configuring computer readable program code devices to cause said computer to balance said preliminary colorant combinations to allow for presence of non-colorant components in said matched coating composition to generate one or more viable combinations optimized in accordance with mixing and regulatory criteria developed for said specified end-use; and
(d) means for configuring computer readable program code devices to cause said computer to select an optimal viable combination from said viable combinations In accordance with an acceptability equation for said specified end-use, said optimal viable combination having an optimal acceptability value for said specified end-use wherein said known colorants and non-colorant components when mixed in accordance with said optimal viable combination produce said matched coating composition that when applied as a matched coating visually matches with appearance of said target coating, wherein said acceptability equation is a summation of acceptability factors multiplied by a weight assigned to each said acceptability factor, wherein said acceptability factors comprise color difference, metamerism, closeness of spectral curve match, durability or cost.

11. The device of claim 10 further comprising means for configuring computer readable program code devices to cause said computer to display on a screen of a monitor of said device said optimal viable combination.

12. The device of claim 10 wherein said device is a transportable device.

13. The device of claim 10 wherein said spectrophotometer is a multiangle spectrophotometer.

14. The device of claim 10 wherein said spectrophotometer is a sphere geometry spectrophotometer.

15. The device of claim 10 further comprising:
(a) means for configuring computer readable program code devices to cause said computer to generate a signal in accordance with said optimal viable combination to dispense said components for making a desired amount of said matched coating composition;
(b) a dispenser for dispensing said components in a container, said dispenser being in communication with said computer;
(c) means for configuring computer readable program code devices to cause said computer to generate a signal upon completion of making said desired amount of said matched coating composition; and
(d) means for configuring computer readable program code devices to cause said computer to generate a signal to said dispenser to stop dispensing of said components.

16. The device of claim 15 further comprising a mixer for mixing said components dispensed in said container.

17. The device of claim 10 or 15 wherein said computer is in communication with a host computer.

18. A method for producing a matched resin for a specified end-use, said method comprising:

(i) measuring reflectances of a target portion of a target substrate at a set of preset wavelengths with a spectrophotometer of a coating characterizing device to plot a target spectral curve of said target portion, wherein said target portion is on an undamaged portion of said target substrate comprising an auto body, plastic substrate or a marine substrate;

(ii) calculating target color (L,a,b or L,C,h) values of said target portion from said target spectral curve of said target portion;

(iii) selecting one or more preliminary colorant combinations from a stored list of known colorants in accordance with a combinatorial selection criteria to match with said target color values, wherein said stored list of known colorants comprises pigments, dispersions, tints, dyes, metallic flakes or a combination thereof, and wherein under said combinatorial selection criteria compriser avoiding shading with complementary colorants and preferring colorant combinations with a fewer number of pigments than a greater number of pigments;

(iv) determining concentrations of each said known colorant in each of said preliminary colorant combinations in accordance with color matching criteria to generate one or more intermediate colorant combinations of said known colorants wherein each of said intermediate colorant combinations is optimized for optimal color match with said target color values;

(v) balancing said intermediate colorant combinations to allow for presence of non-colorant components in said matched coating composition to generate one or more viable combinations of said known colorants, wherein each of said viable combinations is optimized in accordance with mixing and regulatory practices developed for said specified end-use;

(vi) selecting an optimal viable combination from said viable combinations in accordance with an acceptability equation for said specified end-use, said optimal viable combination having an optimal acceptability value for said specified end-use wherein components in said optimal viable combination when mixed produce said matched resin that when formed as a matched substrate visually matches appearance of said target substrate, wherein said acceptability equation is a summation of acceptability factors multiplied by weight assigned to each said acceptability factor, wherein said acceptability factors comprise color difference, metamerism, closeness of spectral curve match, durability or cost; and (vii) displaying on a screen of a monitor of said device said optimal viable combination.

19. The method of claim 18 wherein said matched substrate is a dashboard or interior door panels of an automobile and said target substrate is automobile upholstery.

20. The method of claim 18 wherein said matched substrate is an automobile bumper guard and said target substrate is auto body.

21. The method of claim 18 further comprising:
(a) mixing said components in said optimal viable combination with a resin to produce said matched resin; and
(b) processing said matched resin into said matched substrate.

22. The method of claim 21 wherein said processing step comprises injection molding, blow molding, rotational molding, thermoforming or extruding of said matched resin.

23. A matched resin produced by the method of claim 18.

24. A portable computer usable storage medium having computer readable program code means stored therein for producing a matched coating composition for a specified end-use, said computer readable program code means comprising:

(a) means for configuring computer readable program code devices to cause a computer to select one or more preliminary colorant combinations from a stored list of known colorants in accordance with a combinatorial selection criteria to match with target color values of a target portion on an undamaged portion of a target substrate comprising an auto body, plastic substrate, or a marine substrate, wherein said stored list of known colorants comprises pigments, dispersions, tints, dyes, metallic Rakes or a combination thereof and wherein said combinatorial selection criteria comprise avoiding shading with complementary colorants and preferring colorant combinations with a fewer number of pigments than a greater number of pigments;

(b) means for configuring computer readable program code devices to cause said computer to determine concentration of each said known colorant in each of said preliminary colorant combinations in accordance with color matching criteria wherein said concentration of each said known colorant is optimized for optimal match of color values of each of said preliminary colorant combinations with said target color values;

(c) means for configuring computer readable program code devices to cause said computer to balance said preliminary colorant combinations to allow for presence of non-colorant components in said matched coating composition to generate one or more viable combinations optimized in accordance with mixing and regulatory criteria developed for said specified end-use; and (d) means for configuring computer readable program code devices to cause said computer to select an optimal viable combination from said viable combinations in accordance with an acceptability equation for said specified end-use, said optimal viable combination having an optimal acceptability value for said specified end-use wherein said known colorants and non-colorant components when mixed in accordance with said optimal viable combination produce said matched coating composition that when applied as a matched coating visually matches with the appearance of a target coating, wherein said acceptability equation is a summation of acceptability factors multiplied by a weight assigned to each said acceptability factor, wherein said acceptability factors comprise color difference, metamerism, closeness of spectral curve match, durability or cost.

25. The portable computer usable storage medium of claim 24 further comprising means for configuring computer readable program code devices to cause said computer to display on a screen of a monitor said optimal viable combination.

26. The portable computer usable storage medium of claim 24 further comprising:
(a) means for configuring computer readable program code devices to cause said computer to generate a signal in accordance with said optimal viable combination to dispense said known colorants and said non-colorant components for making a desired amount of said matched coating composition;
(b) a dispenser for dispensing said known colorants and said non-colorant components in a container, said dispenser being in communication with said computer;
(c) means for configuring computer readable program code devices to cause said computer to generate a signal upon completion of making said desired amount of said matched coating composition; and (d) means for configuring computer readable program code devices to cause said computer to generate a signal to said dispenser to stop dispensing of said known colorants and said non-colorant component.

27. The portable computer usable storage medium of claim 24 wherein said medium is CD-Rom.

* * * * *